United States Patent
Song et al.

(10) Patent No.: US 11,459,579 B2
(45) Date of Patent: Oct. 4, 2022

(54) TRANSGENIC PLANTS PRODUCED WITH A K-DOMAIN, AND METHODS AND EXPRESSION CASSETTES RELATED THERETO

(71) Applicant: Board of Trustees of Michigan State University, East Lansing, MI (US)

(72) Inventors: Guo-qing Song, East Lansing, MI (US); Aaron Walworth, East Lansing, MI (US); Dongyan Zhao, Geneva, NY (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 85 days.

(21) Appl. No.: 16/673,055

(22) Filed: Nov. 4, 2019

(65) Prior Publication Data

US 2020/0354733 A1 Nov. 12, 2020

Related U.S. Application Data

(63) Continuation-in-part of application No. 14/903,234, filed as application No. PCT/US2014/045115 on Jul. 1, 2014, now Pat. No. 10,570,409.

(60) Provisional application No. 61/844,248, filed on Jul. 9, 2013.

(51) Int. Cl.
*C12N 15/82* (2006.01)
*C07K 14/415* (2006.01)

(52) U.S. Cl.
CPC .......... *C12N 15/827* (2013.01); *C07K 14/415* (2013.01); *C12N 15/8249* (2013.01); *C12N 15/8261* (2013.01)

(58) Field of Classification Search
None
See application file for complete search history.

(56) References Cited

U.S. PATENT DOCUMENTS

| | | |
|---|---|---|
| 4,873,192 A | 10/1989 | Kunkel |
| 4,945,050 A | 7/1990 | Sanford et al. |
| 5,240,855 A | 8/1993 | Tomes |
| 5,268,463 A | 12/1993 | Jefferson |
| 5,316,931 A | 5/1994 | Donson et al. |
| 5,322,783 A | 6/1994 | Tomes et al. |
| 5,324,646 A | 6/1994 | Buising et al. |
| 5,380,831 A | 1/1995 | Adang et al. |
| 5,399,680 A | 3/1995 | Zhu et al. |
| 5,436,391 A | 7/1995 | Fujimoto et al. |
| 5,466,785 A | 11/1995 | de Framond |
| 5,489,527 A | 2/1996 | Wilson |
| 5,563,055 A | 10/1996 | Townsend et al. |
| 5,565,350 A | 10/1996 | Kmiec |
| 5,569,597 A | 10/1996 | Grimsley et al. |
| 5,583,210 A | 12/1996 | Neill et al. |
| 5,589,367 A | 12/1996 | Donson et al. |
| 5,602,321 A | 2/1997 | John |
| 5,604,121 A | 2/1997 | Hilder et al. |
| 5,605,793 A | 2/1997 | Stemmer |
| 5,608,142 A | 3/1997 | Barton et al. |
| 5,608,144 A | 3/1997 | Baden et al. |
| 5,608,149 A | 3/1997 | Barry et al. |
| 5,659,026 A | 8/1997 | Baszczynski et al. |
| 5,731,181 A | 3/1998 | Kmiec |
| 5,736,369 A | 4/1998 | Bowen et al. |
| 5,756,325 A | 5/1998 | Kmiec |
| 5,760,012 A | 6/1998 | Kmiec et al. |
| 5,792,931 A | 8/1998 | Duvick et al. |
| 5,795,972 A | 8/1998 | Kmiec |
| 5,837,458 A | 11/1998 | Minshull et al. |
| 5,866,785 A | 2/1999 | Donson et al. |
| 5,871,984 A | 2/1999 | Kmiec |
| 5,879,918 A | 3/1999 | Tomes et al. |
| 5,886,244 A | 3/1999 | Tomes et al. |
| 5,889,190 A | 3/1999 | Donson et al. |
| 5,889,191 A | 3/1999 | Turpen |
| 5,891,665 A | 4/1999 | Wilson |
| 5,932,782 A | 8/1999 | Sidney |
| 5,952,544 A | 9/1999 | Browse et al. |
| 5,981,840 A | 11/1999 | Zhao et al. |
| 6,072,050 A | 6/2000 | Bowen et al. |
| 6,177,611 B1 | 1/2001 | Rice |
| 6,232,529 B1 | 5/2001 | Singletary et al. |
| 8,697,947 B2 | 4/2014 | Hatzfeld et al. |
| 2009/0183270 A1* | 7/2009 | Adams ............... C12N 15/8261 800/260 |

(Continued)

FOREIGN PATENT DOCUMENTS

| | | |
|---|---|---|
| EP | 0075444 A2 | 3/1983 |
| WO | 9322443 A1 | 11/1993 |

(Continued)

OTHER PUBLICATIONS

Krizek et al. (Proceedings of the National Academy of Sciences 93.9 (1996): 4063-4070). (Year: 1996).*

Ferrario et al., Ectopic Expression of the Petunia MADS Box Gene UNSHAVEN Accelerates Flowering and Confers Leaf-Like Characteristics to Floral Organs in a Dominant-Negative Manner, Plant Cell. vol. 16, No. 6, pp. 1490-1505 (2004).

Fetter et al., Interactions between Plasma Membrane Aquaporins Modulate Their Water Channel Activity, The Plant Cell vol. 16, pp. 215-228 (2004).

Figge et al., Stringent Regulation of Stably Integrated Chloramphenicol Acetyl Transferase Genes by *E. coli* lac Repressor in Monkey Cells, Cell vol. 52, pp. 713-722 (1988).

(Continued)

*Primary Examiner* — Charles Logsdon
(74) *Attorney, Agent, or Firm* — Westman, Champlin & Koehler, P.A.; Visala C. Goswitz

(57) ABSTRACT

Methods and compositions of improving plant yield by introducing into a plant the K-domain of a MADS box gene are disclosed. The expression of the K-domain provides plants with altered flower development, plant size and leaf development.

20 Claims, 9 Drawing Sheets
(6 of 9 Drawing Sheet(s) Filed in Color)
Specification includes a Sequence Listing.

(56) References Cited

U.S. PATENT DOCUMENTS

2016/0304890 A1    10/2016    Song et al.

FOREIGN PATENT DOCUMENTS

| | | | |
|---|---|---|---|
| WO | 9411516 | A1 | 5/1994 |
| WO | 9849350 | A1 | 11/1998 |
| WO | 9907865 | A1 | 2/1999 |
| WO | 9925821 | A1 | 5/1999 |
| WO | 9925840 | A1 | 5/1999 |
| WO | 9925853 | A1 | 5/1999 |
| WO | 9925854 | A1 | 5/1999 |
| WO | 9925855 | A1 | 5/1999 |
| WO | 9961619 | A1 | 12/1999 |
| WO | 0017364 | A2 | 3/2000 |
| WO | 2015006105 | A1 | 1/2015 |

OTHER PUBLICATIONS

Finer et al., Transformation of Soybean via Particle Bombardment of Embryogenic Suspension Culture Tissue, In Vitro Cell. Dev. Biol. vol. 27P, pp. 175-182 (1991).

Fromm et al., Inheritance and Expression of Chimeric Genes in the Progeny of Transgenic Maize Plants, BioTechnology vol. 8, pp. 833-839 (1990).

Fuerst et al., Transfer of the inducible lac repressor/operator system from *Escherichia coli* to a vaccinia virus expression vector, Proc. Natl. Acad. Sci vol. 86, pp. 2549-2553 (1989).

Gallie et al., The Tobacco Etch Viral 5' Leader and Poly(A) Tail are Functionally Synergistic Regulators of Translation, Gene vol. 165, pp. 233-238 (1995).

Gehrke et al., Untranslated Leader Sequences and Enhanced Messenger RNA Translational Efficiency, Post-Transcriptional Control of Gene Expression, Springer-Verlag Berlin Heidelberg, pp. 389-398 (1990).

Genbank accession 00504309, submitted Apr. 20, 2006.

Gill et al., Negative effect of the transcriptional activator GAL4, Nature vol. 334, pp. 721-724 (1988).

Gossen et al., Tight control of gene expression in mammalian cells by tetracycline-responsive promoters, Proc. Natl. Acad. Sci. vol. 89, pp. 5547-5551 (1992).

Gossen et al., Control of gene activity in higher eukaryotic cells by prokaryotic regulatory elements, TIBS 18, pp. 471-475 (1993).

Greco et al., In Posidonia oceanica cadmium induces changes in DNA methylation and chromatin patterning, J. Exp. Bot. vol. 63, No. 2, pp. 695-709 (2011).

Guerineau et al., Effect of Deletions in the Cauliflower Mosaic Virus Polyadenylation Sequence on the Choice of the Polyadenylation Sites in Tobacco Protoplasts, Mol. Gen. Genel. vol. 226, pp. 141-144 (1991).

Guo et al., Protein Tolerance to Random Amino Acid Change, PNAS vol. 101, No. 25, pp. 9205-9210 (2004).

Henikoff et al., Amino Acid Substitution Matrices from Protein Blocks, Proc. Natl. Acad. Sci. vol. 89, pp. 10915-10919 (1992).

Hepler et al., Nuclear concentration and mitotic dispersion of the essential cell cycle protein, P13suc1, examined in living cells, Proc. Natl. Acad. Sci vol. 91, pp. 2176-2180 (1994).

Heuer et al., The maize MADS box gene ZmMADS3 affects node number and spikelet development and is co-expressed with ZmMADS1 during flower development, in egg cells, and early embryogenesis, Plant Pysiol. vol. 127, No. 1, pp. 33-45 (2001).

Higgins et al., CLUSTAL: A Package for Performing Multiple Sequence Alignment on a Microcomputer, Gene vol. 73, pp. 237-244 (1988).

Higgins et al., Fast and Sensitive Multiple Sequence Alignments on a Microcomputer, Computer Applications in the Biosciences: CABIOS, vol. 5, No. 2, pp. 151-153 (1989).

Hillen et al., Tet Repressor-tet Operator Interaction, Protein-Nucleic Acid Interaction, pp. 143-162 (1989).

Hood et al., New Agrobacterium helper plasmids for gene transfer to plants, Transgenic Research vol. 2, pp. 208-218 (1993).

Hooykaas-Van Slogteren et al., Expression of Ti plasmid genes in monocotyledonous plants infected with Agrobacterium tumefaciens, Nature vol. 311, pp. 763-764 (1984).

Horsch et al., A simple and general method for transferring genes into plants, Science vol. 227, 5 pages (1985).

Hu et al., The Inducible lac Operator-Repressor System Is Functional in Mammalian Cells, Cell vol. 48, pp. 555-566 (1987).

Huang et al., Parallelization of a Local Similarity Algorithm, Computer Applications in the Biosciences vol. 8, No. 2, pp. 155-165 (1992).

Hush et al., Quantification of microtubule dynamics in living plant cells using fluorescence redistribution after photobleaching. Journal of Cell Science vol. 107, pp. 775-784 (1994).

Immink et al., The ABC of MADS domain protein behaviour and interactions, Seminars in Cell & Developmental Biology vol. 21, pp. 87-93 (2010).

Innis et al., Optimization of PCRs, PCR Protocols: A Guide to Methods and Applications, 11 pages (1990).

Iocco et al., Genetic transformation of major wine grape cultivars of *Vitis vinifera* L., Transgenic Research vol. 10, pp. 105-112 (2001).

Ishida et al., High efficiency transformation of maize (*Zea mays* L.) mediated by Agrobacterium tumefaciens, Nature Biotechnology vol. 14, pp. 745-750 (1996).

Jobling et al., Enhanced Translation of Chimaeric Messenger RNAs Containing a Plant Viral Untranslated Leader Sequence, Nature vol. 325, pp. 622-625 (1987).

Jones et al., Isolation of the Tomato Cf-9 Gene for Resistance to Cladosporium fulvum by Transposon Tagging, Science vol. 266, pp. 789-793 (1994).

Jorgensen et al., Chaicone synthase cosuppression phenotypes in petunia flowers: comparison of sense vs. antisense constructs and single-copy vs complex T-DNA sequences, Plant Molecular Biology vol. 31, pp. 957-973 (1996).

Joshi, Putative Polyadenylation Signals in Nuclear Genes of Higher Plants: a Compilation and Analysis, Nucleic Acids Research vol. 15, No. 23, pp. 9627-9640 (1987).

Kaeppler et al., Silicon carbide fiber-mediated DNA delivery into plant cells, Plant Cell Reports vol. 9, pp. 415-418 (1990).

Kaeppler et al., Silicon carbide fiber-mediated stable transformation of plant cells, Theor Appl Genet vol. 84, pp. 560-566 (1992).

Karlin et al., Applications and Statistics for Multiple High-Scoring Segments in Molecular Sequences, Proc. Natl. Acad. Sci. vol. 87, pp. 2264-2268 (1990).

Karlin, Methods for Assessing the Statistical Significance of Molecular Sequence Features by Using General Scoring Schemes, Proc. Natl. Acad. Sci. vol. 90, pp. 5873-5877 (1993).

Kato et al., Spectral Profiling for the Simultaneous Observation of Four Distinct Fluorescent Proteins and Detection of Protein-Protein Interaction via Fluorescence Resonance Energy Transfer in Tobacco Leaf Nuclei, Plant Physiol vol. 129, pp. 931-942 (2002).

Kaufmann et al., MIKC-type MADS-domain proteins: structural modularity, protein interactions and network evolution in land plants, Gene vol. 347, pp. 183-198 (2005).

Klein et al., Factors Influencing Gene Delivery Into *Zea mays* Cells By High-Velocity Microprojectiles, BioTechnology vol. 6, pp. 559-563 (1988).

Klein et al., Transfer of foreign genes into intact maize cells with high-velocity microprojectiles, Proc. Natl. Acad. Sci. vol. 85, pp. 4305-4309 (1988).

Klein et al., Genetic Transformation of Maize Cells by Particle Bombardment, Plant Physiol. vol. 91, pp. 440-444 (1989).

Kleinschmidt et al., Dynamics of Repressor-Operator Recognition: The Tn10-Encoded Tetracycline Resistance Control, Biochemistry vol. 27, pp. 1094-1104 (1988).

Kojima et al., Buckwheat Transformed with CDNA of a Rice MADS Box Gene is Stimulated in Branching, Plant Biotechnology vol. 17, No. 1, pp. 35-42 (2000).

Kunkel et al., Rapid and Efficient site-specific mutagenesis without phenotypic selection, Proc. Natl. Acad. Sci vol. 82, pp. 488-492 (1985).

(56) References Cited

OTHER PUBLICATIONS

Kunkel et al., Rapid and Efficient Site-Specific Mutagenesis without Phenotypic Selection, Methods in Enzymology vol. 154, pp. 367-382(1987).

Kwantes et al., How MIKC* MADS-Box Genes Originated and Evidence for Their Conserved Function Throughout the Evolution of Vascular Plant Gametophytes, Mol. Biol. Evol. vol. 29, No. 1, pp. 293-302 (2011).

Labow et al., Conversion of the lac Repressor into an Allosterically Regulated Transcriptional Activator for Mammalian Cells, Molecular and Cellular Biology, pp. 3343-3356 (1990).

Last et al., pEmu: An Improved Promoter for Gene Expression in Cereal Cells, Theor Appl Genet vol. 81, pp. 581-588 (1991).

Li et al., An improved rice transformation system using the biolistic method, Plant Cell Reports vol. 12, pp. 250-255 (1993).

Lim et al., Two rice MADS domain proteins interact with OsMADSI, Plant Molecular Biology vol. 44, pp. 513-527 (2000).

Lommel et al., Identification of the Maize Chlorotic Mottle Virus Capsid Protein Cistron and Characterization of its Subgenomic Messenger RNA, Virology vol. 181, pp. 382-385 (1991).

Macejak et al., Internal Initiation of Translation Mediated by the 5' Leader of a Cellular mRNA, Nature vol. 353, pp. 90-94 (1991).

Martin et al., Map-Based Cloning of a Protein Kinase Gene Conferring Disease Resistance in Tomato, Science vol. 262, No. 5138, pp. 1432-1436 (1993).

McCabe et al., Stable Transformation of Soybean (Glycine Max) by Particle Acceleration, BioTechnology vol. 6, pp. 923-926 (1988).

McCormick et al., Leaf disc transformation of cultivated tomato (*L. esculentum*) using Agrobacterium tumefaciens, Plant Cell Reports vol. 5, pp. 81-84 (1986).

McElroy et al., Isolation of an Efficient Actin Promoter for Use in Rice Transformation, The Plant Cell vol. 2, pp. 163-171 (1990).

Meinkoth et al., Hybridization of Nucleic Acids Immobilized on Solid Supports, Analytical Biochemistry vol. 138, pp. 267-284 (1984).

Mindrinos et al., The A. thaliana Disease Resistance Gene RPS2 Encodes a Protein Containing a Nucleotide-Binding Site and Leucine-Rich Repeats, Cell vol. 78, pp. 1089-1099 (1994).

Mogen et al., Upstream Sequences Other than AAUAAA Are Required for Efficient Messenger RNA 3'-End Formation n Plants, The Plant Cell vol. 2, pp. 1261-1272 (1990).

Moore et al., Strategies for the in vitro Evolution of Protein Function: Enzyme Evolution by Random Recombination of mproved Sequences, J. Mol. Biol. vol. 272, pp. 336-347 (1997).

Munroe et al., Tales of Poly(A): A Review, Gene vol. 91, pp. 151-158 (1990).

Murashige et al., A Revised Medium for Rapid Growth and Bio Assays with Tobacco Tissue Cultures, Physiologia Plantarum vol. 15, pp. 473-497 (1962).

Murray et al., Codon Usage in Plant Genes, Nucleic Acids Research vol. 17, No. 2, pp. 477-498 (1989).

Myers et al., Optimal alignments in linear space, CABIOS vol. 4, No. 1, pp. 11-17 (1988).

Needleman et al., A General Method Applicable to the Search for Similarities in the Amino Acid Sequence of Two Proteins, J. Mol. Biol. vol. 48, pp. 443-453 (1970).

NeSmith, Fruit Development Period of Several Rabbiteye Blueberry Cultivars, Proc. VIII International Symposium on Vaccinium Culture, vol. 715, pp. 137-142, 2006.

Nomura et al., Embryogenesis from Microinjected Single Cells in a Carrot Cell Suspension Culture, Plant Science vol. 14, pp. 53-58 (1986).

Ddell et al., Identification of DNA Sequences Required for Activity of the Cauliflower Mosaic Virus 35S Promoter, Nature vol. 313, pp. 810-812 (1985).

Oliva et al., Evidence That Tetracycline Analogs Whose Primary Target is not the Bacterial Ribosome Cause Lysis of *Escherichia coli*, Antimicrobial Agents and Chemotherapy vol. 36, No. 5, pp. 913-919 (1992).

Owens, Grapes, Temperate Fruit Crop Breeding, Springer Netherlands, pp. 197-233 (2008).

Paszkowski et al., Direct gene transfer to plants, The EMBO Journal vol. 3, No. 12, pp. 2717-2722 (1984).

Pearson et al., Improved Tools for Biological Sequence Comparison, Proc. Natl. Acad. Sci. vol. 85, pp. 2444-2448 (1988).

Pearson, Using the FASTA Program to Search Protein and DNA Sequence Databases, Methods in Molecular Biology vol. 25, pp. 365-389 (1994).

Porta et al., Use of Viral Replicons for the Expression of Genes in Plants, Molecular Biotechnology vol. 5, pp. 209-221 (1996).

Proudfoot, Poly(A) Signals, Cell vol. 64, pp. 671-674 (1991).

Reines et al., Elongation Factor Sil-Dependent Transcription by RNA Polymerase II through a Sequence-Specific DNA-Binding Protein, Proc. Natl. Acad. Sci vol. 90, pp. 1917-1921 (1993).

Reznikoff, The Lactose Operon-Controlling Elements: A Complex Paradigm, Molecular Microbiology vol. 6, No. 17, pp. 2419-2422 (1992).

Riggs et al., Stable Transformation of Tobacco by Electroporation: Evidence for Plasmid Concatenation, Proc. Natl. Acad. Sci vol. 83, pp. 5602-5606 (1986).

Rosin et al., Suppression of a vegetative MADS box gene of potato activates axillary meristem development, Plant Physiology vol. 131, pp. 1613-1622 (2003).

Sanfacon et al., A Dissection of the Cauliflower Mosaic Virus Polyadenylation Signal, Genes & Development vol. 5, pp. 141-149 (1991).

Sanford et al., Delivery of Substances into Cells and Tissues Using a Particle Bombardment Process, Particulate Science and Technology vol. 5, pp. 27-37 (1987).

Schubert et al., Cloning of the Alcaligenes Eutrophus Genes for Synthesis of Poly-Beta-Hydroxybutyric Acid (PHB) and Synthesis of PHB in *Escherichia coli*, Journal of Bacteriology vol. 170, No. 12, pp. 5837-5847 (1988).

Singh et al., Cytological Characterization of Transgenic Soybean, Theor. Appl. Genet. vol. 96, pp. 319-324 (1998).

Smaczniak et al., Characterization of MADS-domain transcription factor complexes in *Arabidopsis* flower development, PNAS vol. 109, No. 5, pp. 1560-1565 (2012).

Smaczniak et al., Developmental and evolutionary diversity of plant MADS-domain factors: insights from recent studies, Development vol. 139, pp. 3081-3098 (2012).

Smith et al., Comparison of Biosequences, Advances in Applied Mathematics vol. 2, pp. 482-489 (1981).

Song et al., Agrobacterium Tumefaciens-Mediated Transformation of Blueberry (*Vaccinium corymbosum* L.), Plant Cell. Rep. vol. 23, pp. 475-484 (2004).

Song et al., Constitutive Expression of the K-Domain of a Vaccinium Corymbosum SOC1-like (VcSOC1-K) MADS-Box Gene is Sufficient to Promote Flowering in Tobacco, Plant Cell Reports, ISSN 0721-7714, 10 pages (2013).

Sreekantan et al., VvFT and VvMADS8, the grapevine homologues of the floral integrators FT and SOC1, have unique expression patterns in grapevine and hasten flowering in *Arabidopsis*, Functional Plant Biology vol. 33, pp. 1129-1139 (2006).

Stemmer, Rapid Evolution of A Protein in vitro by DNA Shuffling, Nature vol. 370, pp. 389-391 (1994).

Stemmer, DNA Shuffling by Random Fragmentation and Reassembly: In vitro Recombination for Molecular Evolution, Proc. Natl. Acad. Sci vol. 91, pp. 10747-10751 (1994).

Su et al., High-Level Secretion of Functional Green Fluorescent Protein From Transgenic Tobacco Cell Cultures: Characterization and Sensing, Biotechnology and Bioengineering vol. 85, No. 6, pp. 610-619 (2004).

Tamura et al., MEGA5: Molecular Evolutionary Genetics Analysis Using Maximum Likelihood, Evolutionary Distance, and Maximum Parsimony Methods, Mol. Biol. Evol. vol. 28, No. 10, pp. 2731-2739 (2011).

Thompson et al., CLUSTAL W: Improving the Sensitivity of Progressive Multiple Sequence Alignment Through Sequence weighting, Position-Specific Gap Penalties and Weight Matrix Choice, Nucleic Acids Research vol. 22, No. 22, pp. 4673-4680 (1994).

(56) References Cited

OTHER PUBLICATIONS

Van Dijk et al., Sequence Motifs in MADS Transcription Factors Responsible for Specificity and Diversification of Protein-Protein Interaction, PLOS Computational Biology vol. 6, No. 11, 14 pages (2010).
Velten et al., Isolation of a Dual Plant Promoter Fragment from the Ti Plasmid of Agrobacterium tumefaciens, the EMBO Journal vol. 3, No. 12, pp. 2723-2730 (1984).
Advisory Action dated Apr. 3, 2018 for corresponding U.S. Appl. No. 14/903,234, 3 pages.
Final Rejection dated Dec. 29, 2019 for corresponding U.S. Appl. No. 14/903,234, 13 pages.
Applicant-Initiated Interview Summary dated Mar. 7, 2018 for corresponding U.S. Appl. No. 14/903,234, 3 pages.
Applicant-Initiated Interview Summary dated Apr. 3, 2018 for corresponding U.S. Appl. No. 14/903,234, 2 pages.
Applicant-Initiated Interview Summary dated Mar. 15, 2019 for corresponding U.S. Appl. No. 14/903,234, 2 pages.
Applicant-Initiated Interview Summary dated Jul. 8, 2019 for corresponding U.S. Appl. No. 14/903,234, 1 page.
Notice of Allowance dated Jul. 8, 2019 for corresponding U.S. Appl. No. 14/903,234, 10 pages.
Office Action dated Jun. 9, 2017 for corresponding U.S. Appl. No. 14/903,234, 19 pages.
Office Action dated Dec. 31, 2018 for corresponding U.S. Appl. No. 14/903,234, 18 pages.
Office Action dated Aug. 30, 2016 for corresponding Canadian Application Serial No. 2,917,103, 6 pages.
Office Action dated Aug. 25, 2017 for corresponding Canadian Application Serial No. 2,917,103, 4 pages.
Office Action dated Oct. 12, 2018 for corresponding Canadian Application Serial No. 2,917,103, 3 pages.
International Search Report dated Oct. 10, 2014 for corresponding PCT Application Serial No. PCT/US2014/045115, 6 pages.
Notification Concerning Transmittal of International Preliminary Report on Patentability and Written Opinion dated Jan. 21, 2016 for corresponding PCT Application Serial No. PCT/US2014/045115, 10 pages.
Allison et al., The Nucleotide Sequence of the Coding Region of Tobacco Etch Virus Genomic RNA: Evidence for the Synthesis of a Single Polyprotein, Virology 154, pp. 9-20 (1986).
Altschul et al., Basic Local Alignment Search Tool, J. Mol. Biol. 215, pp. 403-410 (1990).
Altschul et al., Gapped BLAST and PSI-BLAST: A New Generation of Protein Database Search Programs, Nucleic Acids Research vol. 25, No. 17, pp. 3389-3402 (1997).
Amasino et al., The Timing of Flowering, Future Perspectives in Plant Biology, Plant Physiology, vol. 154, pp. 516-520 (2010).
Ausubel et al., Current Protocols in Molecular Biology, Chapter 2-Preparatiopn and Analysis of DNA (Greene Publishing and Wiley-Interscience, New York), 161 pages (2003).
Baim et al., A chimeric mammalian transactivator Based on the lac Repressor that is Regulated by Temperature and Isopropyl Beta-D-thiogalactopyranoside, Proc. Natl. Acad. Sci. vol. 88, pp. 5072-5076 (1991).
Ballas et al., Efficient Functioning of Plant Promoters and Poly(A) Sites in Xenopus Oocytes, Nucleic Acids Research vol. 17, No. 19, pp. 7891-7903 (1989).
Barkley et al., Repressor Recognition of Operator and Effectors, Operator and Effector Binding, pp. 177-220 (1980).
Beetham et al., A Tool for Functional Plant Genomics: Chimeric RNA/DNA Oligonucleotides Cause in vivo Gene-Specific Mutations, Proc. Natl. Acad. Sci. vol. 96, pp. 8774-8778 (1999).
Bolte et al., The N-myristoylated Rab-GTPase m-Rabmc is involved in post-Golgi trafficking events to the lytic vacuole in plant cells, Journal of Cell Science vol. 117, No. 6, pp. 943-954 (2004).
Brown et al., lac Repressor Can Regulate Expression from a Hybrid SV40 Early Promoter Containing a lac Operator in Animal Cells, Cell vol. 49, pp. 603-612 (1987).
Bytebier et al., T-DNA organization in tumor cultures and transgenic plants of the monocotyledon Asparagus officinalis, Proc. Natl. Acad. Sci. vol. 84, pp. 5345-5349 (1987).
Campbell et al., Codon Usage in Higher Plants, Green Algae, and Cyanobacteria, Plant Physiol vol. 92, pp. 1-11 (1990).
Christensen et al., Sequence Analysis and Transcriptional Regulation by Heat Shock of Polyubiquitin Transcripts from Maize, Plant Molecular Biology vol. 12: pp. 619-632 (1989).
Christensen et al., Maize Polyubiquitin Genes: Structure, Thermal Perturbation of Expression and Transcript Splicing, and Promoter Activity Following Transfer to Protoplasts by Electroporation, Plant Molecular Biology vol. 18, pp. 675-689 (1992).
Christopherson et al., Ecdysteroid-dependent regulation of genes in mammalian cells by a *Drosophila ecdysone* receptor and chimeric transactivators, Proc. Natl. Acad. Sci vol. 89, pp. 6314-6318 (1992).
Christou et al., Stable Transformation of Soybean Callus by DNA-Coated Gold Particles, Plant Physiol. vol. 87, pp. 671-674 (1988).
Christou et al., Parameters Influencing Stable Transformation of Rice Immature Embryos and Recovery of Transgenic Plants using Electric Discharge Particle Acceleration, Annals of Botany vol. 75, pp. 407-413 (1995).
Corpet, Multiple Sequence Alignment with Hierarchical Clustering, Nucleic Acids Research vol. 16, No. 22 pp. 10881-10890 (1988).
Crameri et al., Molecular Evolution of an Arsenate Detoxification Pathway by DNA Shuffling, Nature Biotechnology, vol. 15, pp. 436-438 (1997).
Crameri et al., DNA Shuffling of a Family of Genes from Diverse Species Accelerates Directed Evolution, Nature vol. 391, pp. 288-291 (1998).
Crossway et al., Micromanipulation Techniques in Plant Biotechnology, BioTechniques vol. 4, No. 4, pp. 320-334 (1986).
Datta et al., Genetically Engineered Fertile Indica-Rice Recovered from Protoplasts, BioTechnology vol. 8, pp. 736-740 (1990).
Dayhoff et al., A Model of Evolutionary Change in Proteins, Atlas of Protein Sequence and Structure, pp. 345-352 (1978).
Degenkolb et al., Structural Requirements of Tetracycline-Tet Repressor Interaction: Determination of Equilibrium Binding Constants for Tetracycline Analogs with the Tet Repressor, Antimicrobial Agents and Chemotherapy vol. 35, No. 8, pp. 1591-1595 (1991).
Della-Cioppa, Protein Trafficking in Plant Cells, Plant Physiol. vol. 84, pp. 965-968 (1987).
De Pater et al., The Promoter of the Rice Gene GOS2 is Active in Various Different Monocot Tissues and Binds Rice Nuclear Factor ASF-1, The Plant Journal vol. 2, No. 6, pp. 837-844 (1992).
Deuschle, Regulated expression of foreign genes in mammalian cells under the control of coliphage T3 RNA polymerase and lac repressor, Proc. Natl. Acad. Sci vol. 86, pp. 5400-5404 (1989).
Deuschle et al., RNA Polymerase II Transcription Blocked by *Escherichia coli* Lac Repressor, Science vol. 248, pp. 480-483 (1990).
De Wet et al., Exogenous Gene Transfer in Maize (*Zea mays*) using DNA-Treated Pollen, Exogenous Gene Transfer in Maize, pp. 197-209 (1985).
D'Halluin et al., Transgenic Maize Plants by Tissue Electroporation, The Plant Cell vol. 4, pp. 1495-1505 (1992).
Dhanaraj et al., Analysis of gene expression associated with cold acclimation in blueberry floral buds using expressed sequence tags, Plant Science vol. 166, pp. 863-872 (2004).
Doyle et al., A Rapid DNA Isolation Procedure For Small Quantities Of Fresh Leaf Tissue, Phytochemical Bulletin vol. 19, No. 1, pp. 11-15 (1987).
Elroy-Stein et al., Cap-Independent Translation of mRNA Conferred by Encephalomyocarditis Virus 5' Sequence Improves the Performance of the Vaccinia Virus/Bacteriophage T7 Hybrid Expression System, Proc. Natl. Acad. Sci. vol. 86, pp. 6126-6130 (1989).
Walworth et al., Ectopic AtCBF3 Expression Improves Freezing Tolerance and Promotes Compact Growth Habit in Petunia, Mol. Breeding, 11 pages (2013).
Weising et al., Foreign Genes in Plants: Transfer, Structure, Expression, and Applications, Annu. Rev. Genet. vol. 22, pp. 421-477 (1988).

(56) References Cited

OTHER PUBLICATIONS

Wyborski et al., Analysis of Inducers of the *E.coli* Lac Repressor System in Mammalian Cells and Whole Animals, Nucleic Acids Research vol. 19, No. 17, pp. 4647-4653 (1991).
Yang et al., The K Domain Mediates Heterodimerization of the *Arabidopsis* Floral Organ Identity Proteins, APETALA3 and PISTILLATA, The Plant Journal vol. 33, pp. 47-59 (2003).
Yao et al., *Drosophila* Ultraspiracle Modulates Ecdysone Receptor Function via Heterodimer Formation, Cell vol. 71, pp. 63-72 (1992).
Yarranton, Inducible Vectors for Expression in Mammalian Cells, Current Opinion in Biotechnology vol. 3, pp. 506-511 (1992).
Zambetti et al., A Mutant p53 Protein is Required for Maintenance of the Transformed Phenotype in Cells Transformed with p53 Plus ras cDNAs, Proc. Natl. Acad. Sci. vol. 89, pp. 3952-3956 (1992).
Zhang et al., Directed Evolution of a Fucosidase from a Galactosidase by DNA Shuffling and Screening, Proc. Natl. Acad. Sci. vol. 94, pp. 4504-4509 (1997).
Office Action dated Jul. 10, 2019 for corresponding Canadian Application Serial No. 2,917,103, 4 pages.
Jang et al., Characaterization of Tobacco MADS-box Genes Involved in Floral Initiation, Plant Cell Physiol vol. 43, No. 1, pp. 230-238 (2002).
Kang et al., Characterization of Two Rice MADS Box Genes that Control Flowering Time, Mol. Cells vol. 7, No. 4, pp. 559-566 (1997).
Song, Blueberry (*Vaccinium corymbosum* L ), Chapter 11, Agrobacterium Protocols: vol. 2, Methods in Molecular Biology, vol. 1224, pp. 121-131 (2015).
Song et al., Overexpression of the MADS-box gene K-domain increases the yield potential of blueberry, Plant Science No. 276, pp. 22-31 (2018).

\* cited by examiner

```
SOC1_Vaccinium_corymbosum      EQNMQHLKHEAADMSKKIEHLEVAKRKLLGEGLGSCTFEELIQIEQQLEQ
MADS1_Nicotiana_tabacum        EQNLQHMQHAAASLMKKIELLEESKRKLLGEGLQSCSLVELQQIEKQLER
PTM5_Populus_trichocarpoa      EQNMLQLKEEAASMIKKIEHLEVSKRKLLGECLGSCTVEELQQIEQQLER
PTM5_Populus_tremuloides       EEQNMLQLKEEAASMIKKIEHLEVSKRKLLGECLGSCTIEELQQIEQQLER
SOC1-like_Prunus-mume          DQNMQHKQESSSMMKQIELLEVSKRKLLGEGLGSCSIEELQEIEQQLER
SOC1-like_Malus_x_domestica    EQNMQHLKQEATSMMKQIELLEVSKRKLLGEGLGSCTLAELQEIEDQLEK
SOC1_Arabidopsis_thaliana      EENMQHLKYEAANMMKKIEQLEASKRKLLGEGIGTCSIEELQQIEQQLEK
SOC1_Vitis_vinifera            EHNMQHLKHEAANMAKKIELLEISKRKLLGEGLGSCSIEELQQIEQQLER
SOC1-like_Citrus_sinensis      ERYMQQLKHEIANMIEKIEHIEVSQRKLLGQDLGSRTNEELQELDDQLER
                               :. : ::: :.: ::.:* :* ::***** : : : ** :::.***:

SOC1_Vaccinium_corymbosum      SASTIRARKMQVFREQIEKLKEKEKALEAENAML
MADS1_Nicotiana_tabacum        SVSTIRARKIQVFKEQIERLKEKEKILASENAAIL
PTM5_Populus_trichocarpoa      SVSTIRARKNQVFKEQIELLRQKEKLLAAENARL
PTM5_Populus_tremuloides       SVSTIRARKNQVFKEQIELLKQKEKLLAAENARL
SOC1-like_Prunus-mume          SVSNVRARKTQVFKEQIEQLREKGKALAAENEKL
SOC1-like_Malus_x_domestica    SVYNVRARKSQVFKEQIEQLREKEKLLTAENTRL
SOC1_Arabidopsis_thaliana      SVKCIRARKTQVFKEQIEQLKQKEKALAAENEKL
SOC1_Vitis_vinifera            SVSSIRARKNQVFKEQIEQLKEKEKALAAENAML
SOC1-like_Citrus_sinensis      SLRSIRARKAQLFNEQMGQLKEKERLLLEDNARL
                               *  :**** *:*.**:   *::*  :   :* *
```

FIG. 1B

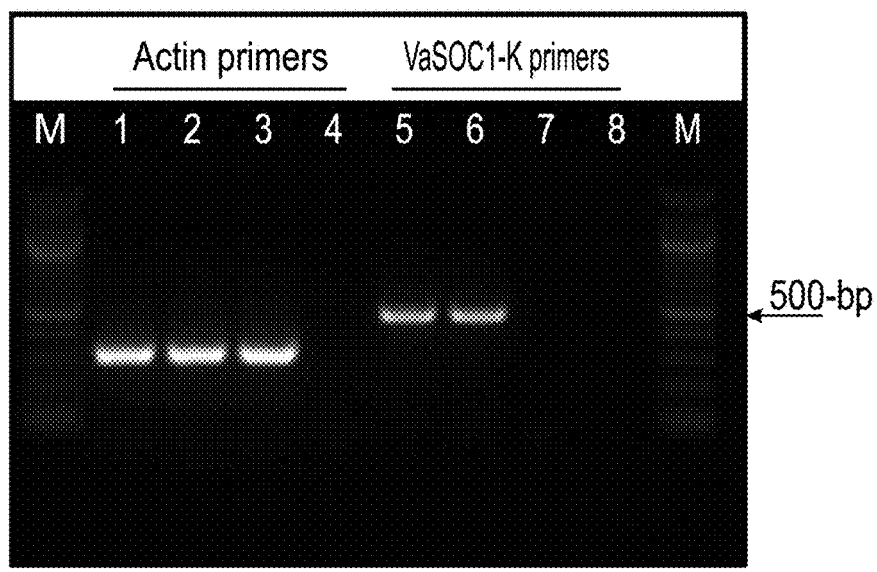

FIG. 2

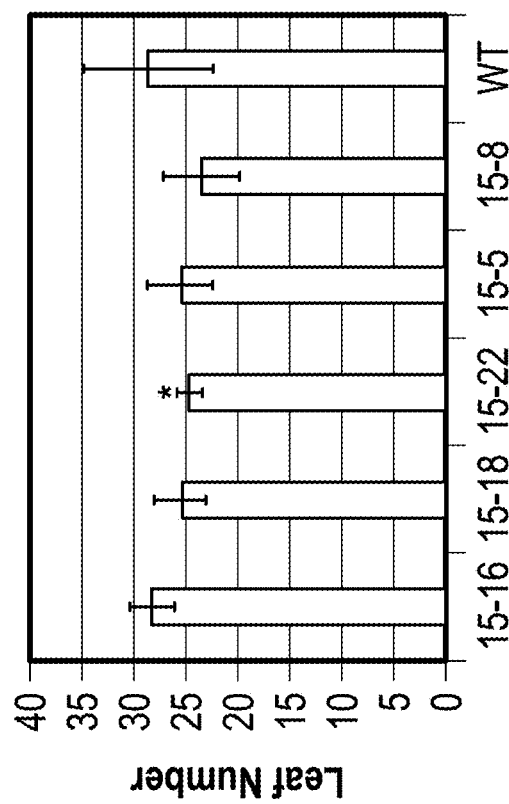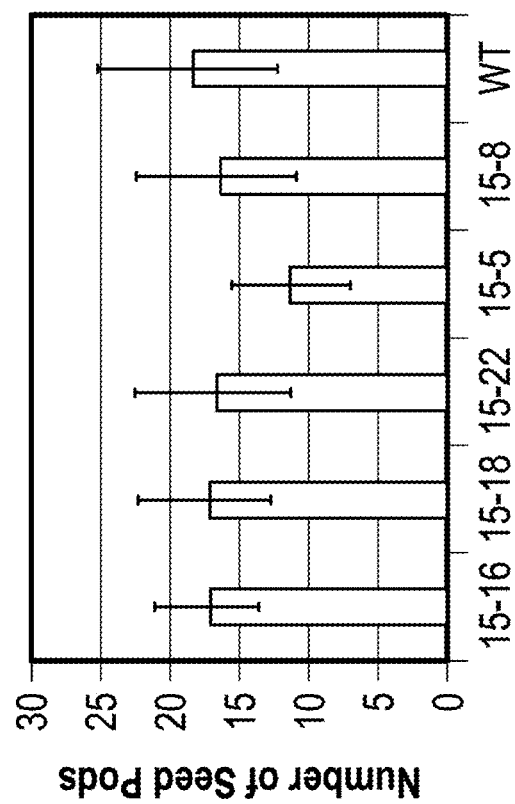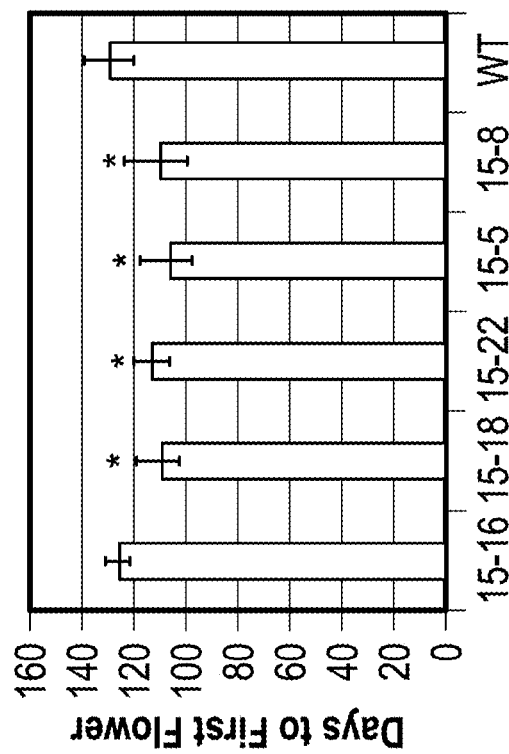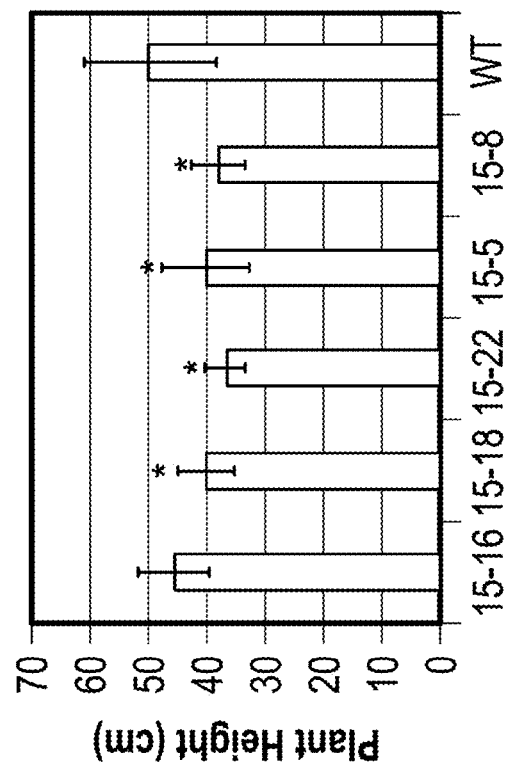

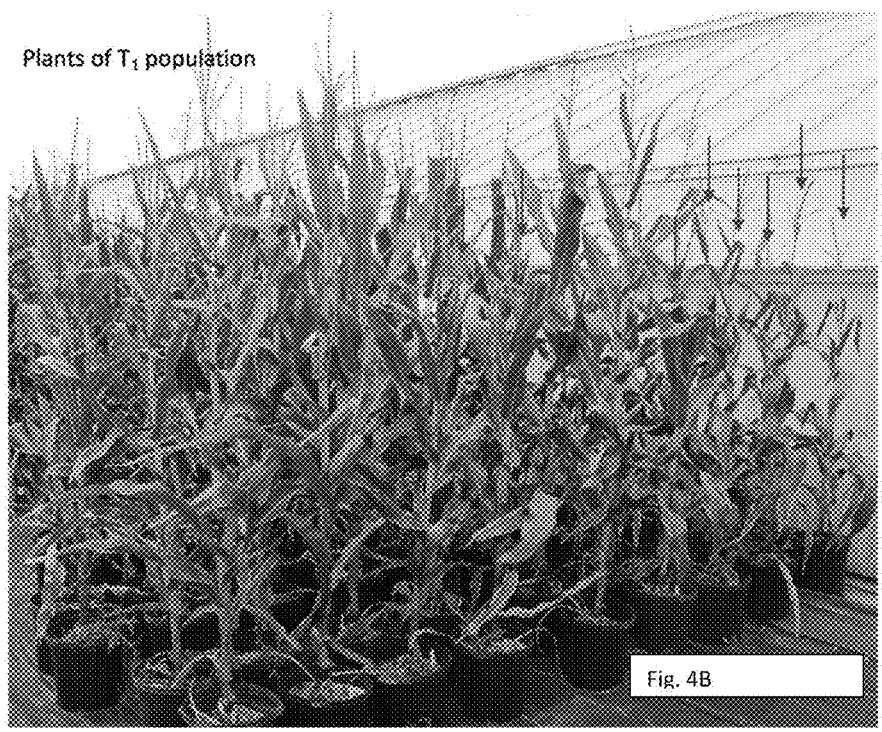
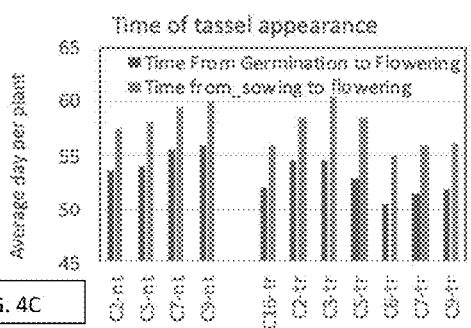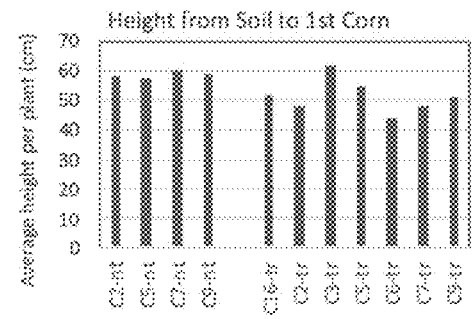
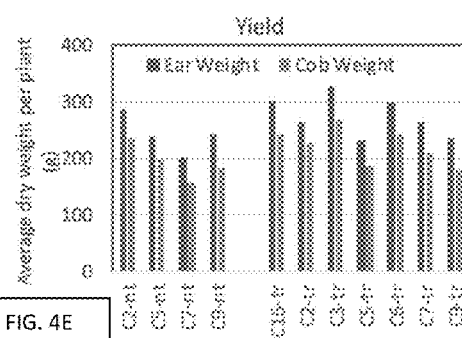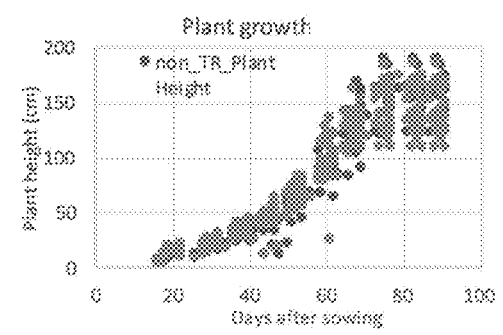

TRANSGENIC PLANTS PRODUCED WITH A K-DOMAIN, AND METHODS AND EXPRESSION CASSETTES RELATED THERETO

RELATED APPLICATIONS

This application is a continuation-in-part of U.S. patent application Ser. No. 14/903,234, filed on Jan. 6, 2016, which application is a U.S. National Stage Filing under 35 U.S.C. 371 from International Application No. PCT/US2014/045115, filed Jul. 1, 2014, and published in English as WO2015/006105 on Jan. 15, 2015, which claims the benefit under 35 U.S.C. 119(e) of U.S. Provisional Application No. 61/844,248, filed on Jul. 9, 2013, which applications and publications are hereby incorporated by reference in their entireties.

BACKGROUND

Food production capacity is faced with an ever-growing number of challenges, including a growing world population, warming globe, and dwindling availability of arable land. In addition, crop yield is a multiple gene-controlled, quantitative trait. The inventors recognize the need for improving crop yield through methods other than traditional breeding.

SUMMARY

The various embodiments described herein provide methods and compositions for increasing plant yield. According to one embodiment a method of increasing yield in a plant relative to a control plant is provided, comprising increasing expression of a K-domain of a MADS polypeptide or variants thereof. In various embodiments the polynucleotide encoding the K-domain polypeptide is set forth in SEQ ID NO: 1, SEQ ID NO: 29, SEQ ID NO: 31, SEQ ID NO: 33, SEQ ID NO: 35 and/or SEQ ID NO: 37. In one embodiment, the K-domain polypeptide is set forth in SEQ ID NO: 2, SEQ ID NO: 30, SEQ ID NO: 32, SEQ ID NO: 34, SEQ ID NO: 36 and/or SEQ ID NO: 38. In other embodiments, an expression cassette useful for producing a transgenic plant is provided. In still other embodiments, transgenic plants transformed with a K-domain polypeptide are provided.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1B is a multiple sequence alignment of the K-domain of SOC1-like proteins according to an embodiment.

FIG. 2 is a digital image of transcriptional analysis of the transgene 35S-VcK-domain and an endogenous actin gene in one nontransgenic (NT) and two randomly selected $T_0$ transgenic tobacco plants according to an embodiment.

FIG. 3C is a graph showing days to emergence of first flowers after the seeds were sown according to an embodiment.

FIG. 3D is a graph showing leaf numbers when 50% of flowers in central cluster were open according to an embodiment.

FIG. 3E is a graph showing plant height at flowering (cm) according to an embodiment.

FIG. 3F is a graph showing number of seed pods in central flower cluster.

FIG. 4B is a digital image of $T_1$ transgenic plants compared with a nontransgenic wild type (WT) plant 102 days after seed sown according to an embodiment.

FIG. 4C is a graph showing days to emergence of first flowers after the seeds were sown according to an embodiment.

FIG. 4D is a graph showing height (cm) from soil to first corn after the seeds were sown according to an embodiment.

FIG. 4E is a graph showing yield according to an embodiment.

FIG. 4F is a graph showing plant height (cm) after the seeds were sown according to an embodiment.

SUBMISSION OF SEQUENCE LISTING

Figure 1A:
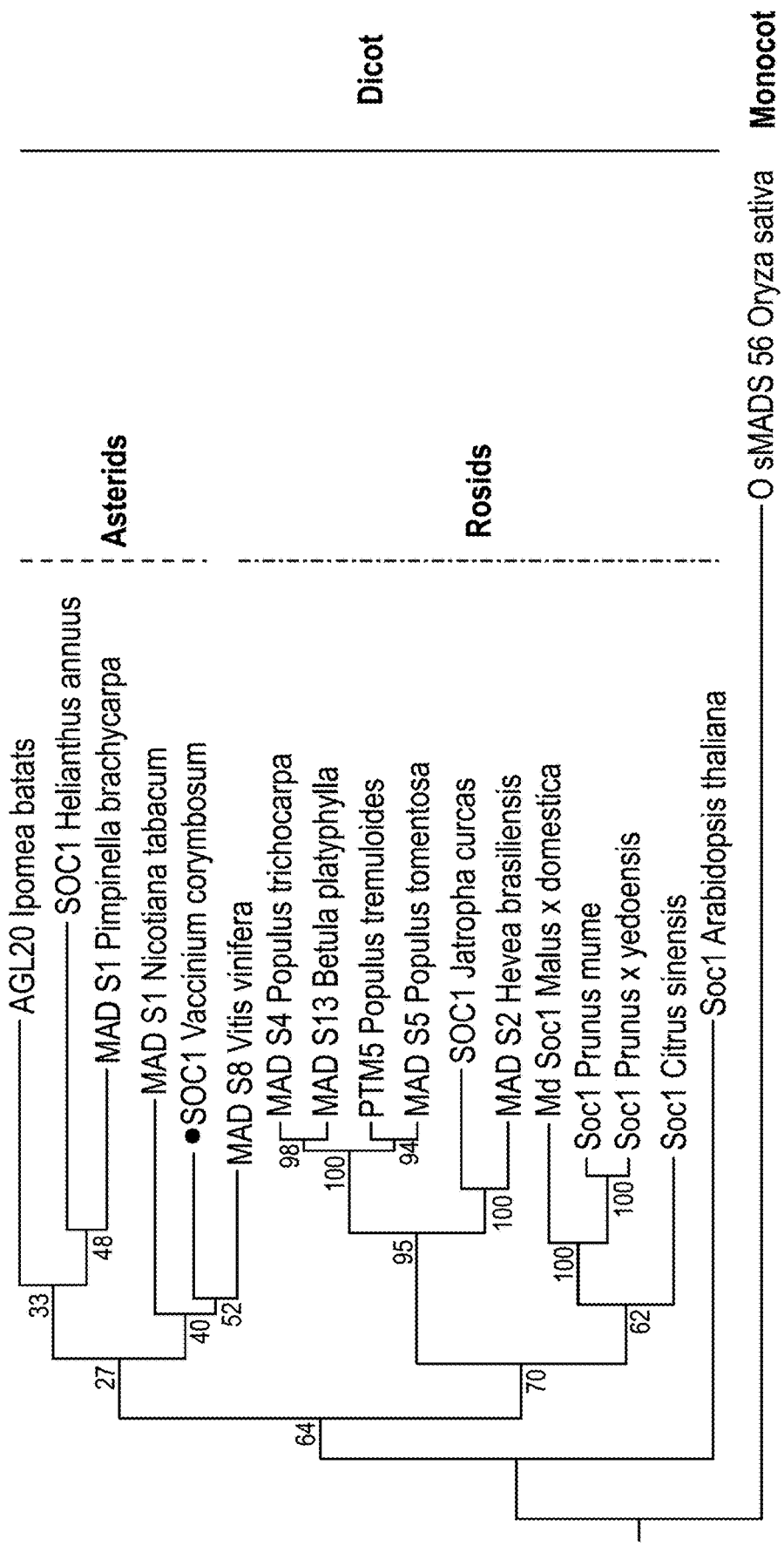
FIG. 1A is a phylogenetic analysis of nucleotide sequences of selected SOC1-like proteins according to an embodiment.

The Sequence Listing associated with this application is filed in electronic format via EFS-Web and hereby incorporated by reference into the specification in its entirety. The name of the text file containing the Sequence Listing is M289.0081US2-SequenceListing.

DETAILED DESCRIPTION

In the following detailed description, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments is defined only by the appended claims.

The term, "comparison window" as used herein refers to sequence relationships between two or more sequences refers to a contiguous and specified segment of a polynucleotide or polypeptide sequence, wherein the sequence in the comparison window may comprise additions or deletions (e.g., gaps) compared to the reference sequence (which does not comprise additions or deletions) for optimal alignment of the two polynucleotides.

The term, "constitutive promoter" as used herein refers to a promoter that is active in transcription during most, but not all plant growth and development phases and under most environmental conditions and in at least one cell, tissue or organ.

The term "control" or "control plant" or "control plant cell" as used herein refers to a reference point for measuring changes in phenotype of a transgenic plant or plant cell. The "control" may include, for example (a) a wild-type plant or cell, e.g., of the same genotype as the starting material for the alteration which resulted in the transgenic plant or cell; (b) a plant or plant cell of the same genotype as the starting material but which has been transformed with a null construct (e.g., with a construct which has no known effect on the trait of interest, such as a construct comprising a marker gene); (c) a plant or plant cell not transformed with the nucleotide or gene of interest; (d) a plant or plant cell which is a non-transformed segregant among progeny of a transgenic plant or plant cell; (e) a plant or plant cell genetically identical to the transgenic plant or plant cell but which is not exposed to conditions or stimuli that would induce the expression of the nucleotide or gene of interest; or (f) the transgenic plant or plant cell itself, under conditions in which the nucleotide or gene of interest is not expressed.

The term "fragment" as used herein refers to a portion of the polynucleotide or a portion of the amino acid sequence. Fragments of a polynucleotide can encode protein fragments that retain the biological activity of the native protein and hence regulate transcription.

The term "grain" as used herein refers to a mature seed produced by commercial growers for purposes other than growing or reproducing the species.

The term, "heterologous" as used herein refers to a sequence that originates from a foreign species, or, if from the same species, is modified from its native form in composition, genomic locus or both by deliberate human intervention.

The term "introducing" as used herein refers to sequences presenting to a plant the polynucleotide or polypeptide in such a manner that the sequence gains access to the interior of a cell of a plant.

The term "isolated" or "purified" as used herein refers to a polynucleotide or polypeptide, protein, or biologically active portion thereof, removed or free from components that normally accompany or interact with the polynucleotide, polypeptide or protein as found in its naturally occurring environment. Thus, an isolated or purified polynucleotide or protein includes a polynucleotide or polypeptide produced by recombinant techniques, or removed from or free of chemical precursors or other chemicals when chemically synthesized.

The term "native" as used herein refers to sequences containing a naturally occurring nucleotide sequence or amino acid sequence.

The term "operably linked" as used herein refers to an expression cassette for plant expression of a functional linkage between two or more elements.

The term "ortholog" as used herein refers to a polynucleotide or polypeptide gene derived from a common ancestral gene and which are found in different species as a result of speciation.

The term "overexpression" or "increased expression" as used herein refers to any form of expression that is additional to the original, wild-type expression level.

The term "percentage of sequence identity" as used herein refers to a polynucleotide's value determined by comparing two optimally aligned sequences over a comparison window, wherein the portion of the polynucleotide sequence in the comparison window may include additions or deletions (e.g., gaps) as compared to the reference sequence (which does not include additions or deletions) for optimal alignment of the two sequences.

The term "plant" as used herein refers to plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

The term "polynucleotide" as used herein refers to polynucleotides comprising DNA. The term includes ribonucleotides and combinations of ribonucleotides and deoxyribonucleotides. Such deoxyribonucleotides and ribonucleotides include both naturally occurring molecules and synthetic analogues. The polynucleotides also encompass all forms of sequences including, but not limited to, single-stranded forms, double-stranded forms, hairpins, stem-and-loop structures, and the like.

The term "reference sequence" as used herein refers to sequence relationships between two or more sequences refers to a subset or the entirety of a specified sequence as a basis for sequence comparison; for example, as a segment of a full-length cDNA or gene sequence, or the complete cDNA or gene sequence.

The terms "sequence identity" or "identity" as used herein refers to relationships between two or more polynucleotides or polypeptides refer to the residues in the two sequences that are the same when aligned for maximum correspondence over a specified comparison window.

The term, "stable transformation" as used herein refers to nucleotides introduced into plants that integrate into the genome of the plant and is capable of being inherited by the progeny thereof.

The terms "stringent conditions" or "stringent hybridization conditions" as used herein refers to conditions under which a probe (nucleotide sequences) will hybridize to its target sequence to a detectably greater degree than to other sequences (e.g., at least 2-fold over background).

The term "tissue-specific promoter" as used herein refers to a promoter that is active in transcription in certain organs or tissues.

The term "trait" as used herein refers to a phenotype derived from a particular sequence or groups of sequences.

The term "transgenic" as used herein refers to a plant or plant part alteration, such as transformation or introduction of a polynucleotide or polypeptide, has occurred, or is a plant or plant cell which is descended from a plant or cell so altered and which has the alteration.

The terms "transient transformation" as used herein refers to a polynucleotide, polypeptide or protein introduced into a plant and does not integrate into the genome of the plant.

The term "variants" as used herein refers to sequences having substantially similar sequences as compared to a first sequence. A variant can include, but is not limited to, a deletion, insertion, substitution or combination thereof of one or more nucleotides or amino acids at one or more internal sites within the native or reference polynucleotide or polypeptide respectively.

The term "yield" as used herein refers to a crop amount that was harvested per unit of land area or the amount of seeds generated from the plant itself or a combination thereof.

Disclosed are methods and compositions of increasing plant yield by expressing the K-domain portion of a gene, such as a MADS-box gene. The K-domain of a MADS-box gene when expressed in plants can increase plant yield compared to a plant not expressing or expressing at lower levels of the K-domain. The molecules may be obtained by any convenient method, whether isolated from a plant or synthetically produced, for example. In one embodiment, methods and compositions are provided to accelerate floral organ development, increase flower numbers, reduce plant size, and reduce leaf numbers, or combinations thereof, without negatively affecting seed or fruit production. The various embodiments provide for methods and compositions which result in improved plant or crop yield by increasing plant density in the field, by reducing plant growth period, or both.

The various embodiments provide for compositions that include the K-domain polynucleotides and polypeptides and variants thereof, or fragment of the MADS-box genes that are involved in accelerating flowering, reducing plant size or leaf numbers or combinations thereof without affecting seed or fruit development. In one embodiment, the SUPPRESSOR OF OVEREXPRESSION OF CONSTANS 1 (SOC1) and SOC1-likes encodes a plant protein with MADS domain and K-domain. MADS-domain transcription factors play essential roles in the evolution of flowering plants through determining floral architecture and regulating flower development. MADS box genes contain a conserved MADS box motif and are often classified into type I and type II subfamilies, in which type II MADS box genes often have conserved K-, I-, and C (Carboxy terminal)-domains. Based on the variations in their K (Keratin)-domains and I (Intervening) domains, the type II MADS box genes are further divided into MIKC$^{nc}$ and MIKC$^c$ (classical MIKC) subgroups, where the latter often have a shorter K domain than that of the MIKC$^{nc}$ and play specific roles in the ABC model of floral development. MIKC$^c$-subgroup consists of 13 major gene clades, of which 12 have been identified and extensively studied in *Arabidopsis thaliana*. Genome-wide analyses of the MIKC$^c$-type MADS box genes have been reported in several plant species, including *Arabidopsis*, tomato (*Solanum lycopersicon*), poplar (*Populus trichocarpa*), rice (*Oryza sativa*), grapevine (*Vitis vinfera*), and cucumber (*Cucumis sativus*). Two gene clades, FLOWERING LOCUS C (FLC) and TM3/K-domain, are major components in the flowering-time pathway. The FLC clade genes, including FLC and FLC-like genes, are central regulators of vernalization-mediated flowering. SOC1 and SOC1-like genes in the TM3/K-domain clade are major flowering pathway integrators, harmonizing flowering signals from multiple pathways. Although there have been many reports on overexpression of intact MIKC$^c$-type MADS box genes, little has been done on the separate domains of these MADS proteins.

In one embodiment, an isolated K-domain of a MADS-box gene (e.g., SOC1-like gene) is disclosed. In one embodiment, the MADS-box gene is from a *Vaccinium corymbosum* (blueberry) (VcK-domain). Overexpression of VcK-domain alone can promote early flowering, reduced plant size or leaf number or combinations thereof without reducing or affecting seed or fruit production. The K-domain nucleotide sequence is shown as SEQ ID NO: 1, the K-domain polypeptide is shown as SEQ ID NO: 2 and the full length MADS-box gene of the SOC1 gene is shown as SEQ ID NO: 3. In other embodiments, other K-domains from MADS-box genes involved in flowering pathways may be used. In various embodiments, LEAFY (LFY) (Accession: AF466801.1), TERMINAL FLOWER 1 (TFL1) (Accession: AF466804.1), APETALA1 (AP1) (Accession: NM_10551.2), LFY-like (contig12297), TFL1-like (contig02213), and AP1-like may be used.

Fragments that are useful as hybridization probes generally do not encode fragment proteins retaining biological activity. Thus, in various embodiments, fragments of a nucleotide sequence may range from at least about 18 nucleotides, about 20 nucleotides, about 50 nucleotides, about 100 nucleotides and up to the full-length polynucleotide encoding the proteins. A fragment of a MADS-box polypeptide can encode a wide number of contiguous amino acids, including, but not limited to, at least 15, 25, 30, 50, 100, 150, 200, 250, 300 or more contiguous amino acids, including any value or range therebetween, or otherwise up to the total number of amino acids present in a full-length MADS domain, or K-domain protein (e.g., SEQ ID NO: 2). In various embodiments, a K-domain polynucleotide or fragments of a MADS domain that includes a K-domain polynucleotide that are useful as hybridization probes, PCR primers, generally need not encode a biologically active portion of a K-domain protein.

In some embodiments, a biologically active portion of a polypeptide having a K-domain, can be prepared by isolating a portion of a K-domain polynucleotide, expressing the encoded portion of the K-domain protein (e.g., by recombinant expression in vitro), and assessing the activity of the encoded portion of the K-domain. In various embodiments, polynucleotides that are fragments of a MADS-box gene or a polynucleotide sequence having a K domain have at least 16, 20, 50, 75, 100, 150, 200, 250, 300, 350, 400, 450, 500, contiguous nucleotides or up to the number of nucleotides present in a full-length K-domain (e.g., SEQ ID NO: 1).

In one embodiment, a biologically active portion of a polypeptide having a maize (*Zea mays*) K-domain, can be prepared by isolating a portion of a maize K-domain polynucleotide, expressing the encoded portion of the maize K-domain protein (e.g., by recombinant expression in vitro), and assessing the activity of the encoded portion of the maize K-domain. In one embodiment, the maize K-domain polynucleotide is as described in SEQUENCE ID NO: 29 and encodes maize K-domain polypeptide as described in SEQUENCE ID NO: 30. In various embodiments, biologically active variants of a maize K-domain will have at least 40%, 45%, 50%, 55%, 60%, 65%, 70%, 75%, 80%, 85%, 90%, 91%, 92%, 93%, 94%, 95%, 96%, 97%, 98%, 99% including any range there between or more sequence identity to the amino acid SEQ ID NO:30

In one embodiment, the maize K-domain polynucleotide is expressed in maize as described below. Expression of the maize K-domain polynucleotide can result in major phenotypic changes such as flowering time, plant height, harvest time, ear weight and/or cob weight. In one embodiment, the maize K-domain polynucleotide is expressed in other plants. Expression of the maize K-domain in tomato plants can result in major phenotypic changes such as, flowering time, plant height, branch number, harvest time, and fruit number.

In one embodiment, a biologically active portion of a polypeptide having a rice (*Oryza sativa*) K-domain, can be prepared by isolating a portion of a rice K-domain polynucleotide, expressing the encoded portion of the rice K-domain protein (e.g., by recombinant expression in vitro), and assessing the activity of the encoded portion of the rice K-domain. In one embodiment, the rice K-domain polynucleotide is as described in SEQUENCE ID NO: 31 that encodes rice K-domain polypeptide as described in SEQUENCE ID NO: 32. In various embodiments, biologically active variants of a rice K-domain will have at least 40%, 45%, 50%, 55%, 60%, 65%, 70%, 75%, 80%, 85%, 90%, 91%, 92%, 93%, 94%, 95%, 96%, 97%, 98%, 99% including any range there between or more sequence identity to the amino acid SEQ ID NO: 32.

In one embodiment, the rice K-domain polynucleotide is expressed in rice. Expression of the rice K-domain polynucleotide can result in major phenotypic changes such as, plant height, time of appearance of first seeds, and/or seed weight per plant. In one embodiment, the rice K-domain polynucleotide is expressed in other plants. Expression of the rice K-domain in tomato plants can result in major phenotypic changes such as, flowering time, plant height, branch number, harvest time, and fruit number.

In one embodiment, a biologically active portion of a polypeptide having a soybean (*Glycine max*) K-domain, can be prepared by isolating a portion of a soybean K-domain polynucleotide, expressing the encoded portion of the soybean K-domain protein (e.g., by recombinant expression in vitro), and assessing the activity of the encoded portion of the soybean K-domain. In one embodiment, the soybean K-domain polynucleotide is as described in SEQUENCE ID NO: 33 that encodes soybean K-domain polypeptide as described in SEQUENCE ID NO:34. In various embodiments, biologically active variants of a soybean K-domain will have at least 40%, 45%, 50%, 55%, 60%, 65%, 70%, 75%, 80%, 85%, 90%, 91%, 92%, 93%, 94%, 95%, 96%, 97%, 98%, 99% including any range there between sequence identity to the amino acid SEQ ID NO:34.

In one embodiment, the soybean K-domain polynucleotide is expressed in other plants, e.g. tomato, as described below. Expression of the soybean K-domain polynucleotide in tomato plants can result in major phenotypic changes such as flowering time, plant height, number of flower clusters, time of appearance of first mature fruit, fruit number, and/or fruit weight per plant. In one embodiment, the soybean K-domain polynucleotide is expressed in soybean plants. Expression of soybean K-domain in soybean plants can result in major phenotypic changes such as, flowering time, plant height, branch number, harvest time, pod number, and/or pod weight per plant.

In one embodiment, a biologically active portion of a polypeptide having a canola (*Brassica napus*) K-domain, can be prepared by isolating a portion of a canola K-domain polynucleotide, expressing the encoded portion of the canola K-domain protein (e.g., by recombinant expression in vitro), and assessing the activity of the encoded portion of the canola K-domain. In one embodiment, the canola K-domain polynucleotide is as described in SEQUENCE ID NO: 35 that encodes canola K-domain polypeptide as described in SEQUENCE ID NO:36. In various embodiments, biologically active variants of a canola K-domain will have at least 40%, 45%, 50%, 55%, 60%, 65%, 70%, 75%, 80%, 85%, 90%, 91%, 92%, 93%, 94%, 95%, 96%, 97%, 98%, 99% including any range there between or more sequence identity to the amino acid SEQ ID NO:36

In one embodiment, the canola K-domain polynucleotide is expressed in canola. Expression of the canola K-domain polynucleotide can result in major phenotypic changes such as flowering time, plant height, number of flower clusters, time of appearance of first pods, pod number, and/or pod weight per plant. In one embodiment, the canola K-domain polynucleotide is expressed in other plants. Expression of the canola K-domain polynucleotide in tomato plants can result in major phenotypic changes such as flowering time, plant height, number of flower clusters, time of appearance of first mature fruit, fruit number, and/or fruit weight per plant.

In one embodiment, a biologically active portion of a polypeptide having a cotton (*Gossypium hirsutum*) K-domain, can be prepared by isolating a portion of a cotton K-domain polynucleotide, expressing the encoded portion of the cotton K-domain protein (e.g., by recombinant expression in vitro), and assessing the activity of the encoded portion of the cotton K-domain. In one embodiment, the cotton K-domain polynucleotide is as described in SEQUENCE ID NO: 37 that encodes cotton K-domain polypeptide as described in SEQUENCE ID NO:38. In various embodiments, biologically active variants of a cotton K-domain will have at least 40%, 45%, 50%, 55%, 60%, 65%, 70%, 75%, 80%, 85%, 90%, 91%, 92%, 93%, 94%, 95%, 96%, 97%, 98%, 99% including any range there between or more sequence identity to the amino acid SEQ ID NO:38.

In one embodiment, the cotton K-domain polynucleotide is expressed in cotton. Expression of the cotton K-domain polynucleotide can result in major phenotypic changes such as flowering time, plant height, number of flower clusters, cottonseed number, and/or cottonseed weight per plant. In one embodiment, the cotton K-domain polynucleotide is expressed in other plants. Expression of the cotton K-domain polynucleotide in tomato plants can result in major phenotypic changes such as flowering time, plant height, number of flower clusters, time of appearance of first mature fruit, fruit number, and/or fruit weight per plant.

Naturally occurring allelic variants can be identified with the use of well-known molecular biology techniques, as, in some embodiments, with polymerase chain reaction (PCR) and hybridization techniques as outlined below. In various embodiments, variant polynucleotides also include synthetically derived polynucleotides, such as those generated, by using site-directed mutagenesis but which still encode a polypeptide having a K-domain that is capable of regulating flowering time, flower numbers, plant size, leaf number or combinations thereof but without affecting seed or fruit development. In various embodiments, variants of a particular polynucleotide may have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide (e.g., a reference polynucleotide) can also be evaluated by comparison of the percent sequence identity between the polypeptide encoded by a variant polynucleotide and the polypeptide encoded by the reference polynucleotide. In various embodiments an isolated polynucleotide that encodes a polypeptide with a given percent sequence identity to the polypeptide of SEQ ID NO: 2 is disclosed. Percent sequence identity between any two polypeptides can be calculated using sequence alignment programs and parameters described elsewhere herein. In some embodiments, the comparison window is at least 20 contiguous nucleotides in length, and optionally can be 30, 40, 50, 100, including any value there between, or longer. Those skilled in the art understand that to avoid a high similarity to a reference sequence due to inclusion of gaps in the polynucleotide sequence a gap penalty is typically introduced and is subtracted from the number of matches. Where any given pair of polynucleotides is evaluated by comparison of the percent sequence identity shared by the two polypeptides they encode, the percent sequence identity between the two encoded polypeptides in some embodiments are at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

Variant proteins encompassed are biologically active, that is, they continue to possess the desired biological activity of the native protein, namely they regulate transcription and result in phenotypes affecting flowering time, plant size and leaf number without affecting seed or fruit production. In various embodiments, such variants may result from genetic polymorphism or from human manipulation. In various embodiments, biologically active variants of a K-domain will have at least about 40%, 45%, 50%, 55%, 60%, 65%, 70%, 75%, 80%, 85%, 90%, 91%, 92%, 93%, 94%, 95%, 96%, 97%, 98%, 99% including any range there between or more sequence identity to the amino acid SEQ ID NO:2 VcK-domain as determined by sequence alignment programs and parameters described elsewhere herein. In various embodiments, a biologically active variant of a K-domain may differ from that protein by as few as 1-15 amino acid residues, as few as 1-10, such as 6-10, including any range there between, to as few as 5, as few as 4, 3, 2 or even 1 amino acid residue.

In various embodiments, the polynucleotides may be altered in various ways including amino acid substitutions, deletions, truncations, and insertions using a variety of methods generally known in the art. In various embodiments, amino acid sequence variants of K-domain or fragments of the MADS-box protein can be prepared by mutations in the DNA by a variety of known methods for mutagenesis and polynucleotide alterations. See, for example, Kunkel (1985) Proc Natl Acad Sci USA 82:488-492; Kunkel, et al., (1987) Methods in Enzymol 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff, et al., (1978) Atlas of Protein Sequence and Structure (Natl. Biomed. Res. Found. Washington, D.C.), herein incorporated by reference. In some embodiments, conservative substitutions, such as exchanging one amino acid with another having similar properties are disclosed.

In various embodiments, genes and polynucleotides include both the naturally occurring sequences as well as mutant forms. Likewise, in other embodiments the proteins encompass naturally occurring proteins as well as variations and modified forms thereof. Such variants will continue to possess the desired activity (e.g., transcription binding that when overexpressed may alter flower development, plant size, leaf number or combinations thereof without affecting seed or fruit development). In various embodiments, the mutations that may be made in the DNA encoding a variant do not place the sequence out of reading frame and do not create complementary regions that could produce secondary mRNA structure. See, DeBoer et al., EP Patent Application Publication Number 75,444A (1983).

In various embodiments, the deletions, insertions, and substitutions of the protein sequences encompassed herein should still retain the characteristics of the protein activity. However, when it is difficult to predict the exact effect of the substitution, deletion, or insertion in advance of doing so, one skilled in the art will appreciate that the effect will be evaluated by routine screening assays. In various embodiments, various methods can be used to assay for the presence of the K-domain, including, directly monitoring the level of expression of a target gene at the nucleotide or polypeptide level. Methods for such an analysis are known and include, for example, Northern blots, protection assays, Western blots, enzymatic or colorimetric assays. In various embodiments, methods to assay for a modulation of transcriptional activity can include monitoring for an alteration in the phenotype of the plant. In some embodiments, modulating the level of the K-domain polypeptide can result in alterations in flower formation, timing, plant height and leaf number.

In various embodiments, variant polynucleotides and proteins also encompass sequences and proteins derived from a mutagenic and recombinogenic procedure such as DNA shuffling. With such a procedure, one or more different K-domain coding sequences can be manipulated to create a new K-domain sequence possessing the desired properties. In this manner, libraries of recombinant polynucleotides are generated from a population of related sequence polynucleotides having sequence regions that have substantial sequence identity and can be homologous recombined in vitro or in vivo. In various embodiments, using this approach, sequence motifs encoding a domain of interest may be shuffled between the K-domain and other K-domains of other known MADS-box genes to obtain a new gene coding for a protein with an improved property of interest, such as an early flowering time, reduced plant height or reduced leaf number or combinations thereof. Strategies for such DNA shuffling are known in the art. See, for example, Stemmer (1994) Proc Natl Acad Sci USA 91:10747-10751; Stemmer (1994) Nature 370:389-391; Crameri, et al, (1997) Nature Biotech 15:436-438; Moore, et al., (1997) J Mol Biol 272:336-347; Zhang, et al., (1997) Proc Natl Acad Sci USA 94:4504-4509; Crameri, et al., (1998) Nature 391:288-291; and U.S. Pat. Nos. 5,605,793 and 5,837,458.

In some embodiments, the polynucleotides can be used to isolate corresponding sequences from other organisms, other plants, or other woody plants. In this manner, methods such as PCR, hybridization, and the like can be used to identify such sequences based on their sequence homology to the sequences set forth herein. Sequences isolated based on their sequence identity to the entire K-domain sequences, set forth herein or to variants and fragments thereof are encompassed herein. In various embodiments, such sequences include sequences that are orthologs of the disclosed sequences. Functions of orthologs are often highly conserved among species. In various embodiments, genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, including any range or value therebetween or greater sequence identity. Thus, isolated polynucleotides that can cause early flowering, reduced plant size or fewer leaves without affecting seed or fruit production per plant and that encodes for a K-domain and which hybridize under stringent conditions to the disclosed K-domain sequences, or to variants or fragments thereof, are encompassed herein.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) Molecular Cloning: A Laboratory Manual (2d ed., Cold Spring Harbor Laboratory Press, Plainview, N.Y.). See also, Innis, et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). In some embodiments, methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (e.g., genomic or cDNA libraries) from a chosen organism. In various embodiments, the hybridization probes may be genomic DNA fragments, cDNA fragments, RNA fragments, or other oligonucleotides. In still other embodiments, the hybridization probes may be labeled with a detectable group such as $^{32}P$, or any other detectable marker. In various embodiments, probes for hybridization can be made by labeling synthetic oligonucleotides based on the K-domain polynucleotide. Methods for preparation of probes for hybridization and for construction of cDNA and genomic libraries are generally known in the art and are disclosed, for example in Sambrook, et al., (1989) Molecular Cloning: A Laboratory Manual (2d ed., Cold Spring Harbor Laboratory Press, Plainview, N.Y.).

In various embodiments, the entire MADS-box domain polynucleotide or one or more portions thereof or a polynucleotide encoding a K domain disclosed herein, may be used as a primer capable of specifically hybridizing to corresponding K-domain polynucleotide and messenger RNAs. To achieve specific hybridization under a variety of conditions, such probes include sequences that are unique among K-domain polynucleotide sequences. In various embodiments, the probes include at least about 10 nucleotides in length, at least about 20 nucleotides in length. Such primer pairs may be used to amplify corresponding K-domain polynucleotide from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Plainview, N.Y.).

Hybridization of such sequences (e.g., Southern blot and Northern blot) may be carried out under stringent conditions. Stringent conditions are sequence-dependent and will be different in different circumstances. By controlling the stringency of the hybridization, washing conditions or both, target sequences that are 100% complementary to the probe can be identified (homologous probing). In other cases, stringency conditions can be adjusted to allow some mismatching in sequences so that lower degrees of similarity are detected (heterologous probing). In various embodiments, a probe is less than about 1000 nucleotides in length, less than 500 nucleotides in length, including any range or value therebetween.

In various embodiments, stringent conditions will be those in which the salt concentration is less than about 1.5 M Na ion, about 0.01 to 1.0 M Na ion concentration (or other salts) at pH 7.0 to 8.3 including any range or value therebetween for both Na concentration and pH, and the temperature is at least 20-35° C. for short probes (e.g., 10 to 50 nucleotides) and at least about 50 to 60° C. for long probes (e.g., greater than 50 nucleotides). Stringent conditions may also be achieved with the addition of destabilizing agents such as formamide. In various embodiments, low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5.X to 1×SSC at 55 to 60° C. In other embodiments high stringency conditions include hybridization in 50% formamide, 1 M NaCl, 1% SDS at 37° C., and a wash in 0.1×SSC at 60 to 65° C. In various embodiments, wash buffers may include about 0.1% to about 1% SDS. In various embodiments, duration of hybridization is less than about 24 hours, about 4 to about 12 hours. The duration of the wash time will be at least a length of time sufficient to reach equilibrium.

Specificity is typically the function of post-hybridization washes, the useful factors being the ionic strength and temperature of the final wash solution. For DNA-DNA hybrids, the $T_m$ can be approximated from the equation of Meinkoth and Wahl (1984) Anal. Biochem. 138:267-284: $T_m=81.5°$ C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. In various embodiments, if sequences with .gtoreq.90% identity are sought, the $T_m$ can be decreased by about 10° C. In various embodiments, stringent conditions are selected to be about 5° C. lower than the thermal melting point ($T_m$) for the specific sequence and its complement at a defined ionic strength and pH. In various embodiments, severely stringent conditions can utilize a hybridization and/or wash at 1, 2, 3 or 4° C. including any range or value therebetween lower than the thermal melting point ($T_m$); In various embodiments, moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. including any range or value therebetween lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), in various embodiments to increase the SSC concentration so that a higher temperature can be used. An extensive guide to the hybridization of nucleic acids may be found in Tijssen (1993) Laboratory Techniques in Biochemistry and Molecular Biology-Hybridization with Nucleic Acid Probes, Part I, Chapter 2 (Elsevier, New York); and Ausubel, et al., eds. (1995) Current Protocols in Molecular Biology, Chapter 2 (Greene Publishing and Wiley-Interscience, New York). See, Sambrook, et al., (1989) Molecular Cloning: A Laboratory Manual (2d ed., Cold Spring Harbor Laboratory Press, Plainview, N.Y.).

Methods of alignment of nucleotide (DNA and RNA) or protein sequences for comparison are well known in the art. Thus, the determination of percent sequence identity between any two sequences can be accomplished using a mathematical algorithm. In various embodiments, a portion of the polynucleotide sequence in a comparison window includes additions or deletions (e.g., gaps) as compared to the reference sequence (which does not include additions or deletions) for optimal alignment of the two sequences.

In various embodiments, the sequence alignment is by Maximum Likelihood method based on the Tamura-Nei model using the MEGA 5 program. In various embodiments, mathematical algorithms are the algorithm of Myers and Miller (1988) CABIOS 4:11-17; the local alignment algorithm of Smith, et al., (1981) Adv Appl Math 2:482; the global alignment algorithm of Needleman and Wunsch (1970) J Mol Biol 48:443-453; the search-for-local alignment method of Pearson and Lipman (1988) Proc Natl Acad Sci 85:2444-2448; the algorithm of Karlin and Altschul (1990) Proc Natl Acad Sci USA 872264, modified as in Karlin and Altschul (1993) Proc Natl Acad Sci USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) Gene 73:237-244 (1988); Higgins, et al., (1989) CABIOS 5:151-153; Corpet, et al., (1988) Nucleic Acids Res 16:10881-90; Huang, et al., (1992) CABIOS 8:155-65; and Pearson, et al., (1994) Meth Mol Biol 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul, et al., (1990) J Mol Biol 215:403 are based on the algorithm of Karlin and Altschul (1990) supra. BLAST nucleotide searches can be performed with the BLASTN program, score=100, word length=12, to obtain nucleotide sequences homologous to a nucleotide sequence encoding a protein. BLAST protein searches can be performed with the BLASTX program, score=50, word length=3, to obtain amino acid sequences homologous to a protein or polypeptide.

To obtain gapped alignments for comparison purposes, Gapped BLAST (in BLAST 2.0) can be utilized as described in Altschul, et al., (1997) Nucleic Acids Res 25:3389. In other cases, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

Unless otherwise stated, pairwise sequence identity/similarity values provided herein refer to the value obtained using the GAP program, which is part of GCG 11.0 using the following parameters: % identity and % similarity using gap creation penalty of 10, gap extension penalty of 1; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP.

GAP uses the algorithm of Needleman and Wunsch (1970) J Mol Biol 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. In various embodiments, for nucleotide sequences the default gap creation penalty is 50 while the default gap extension penalty is 3. The gap creation and gap extension penalties can be expressed as an integer selected from the group of integers that include from 0 to 200. Thus, in various embodiments, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.5, the similarity threshold. The scoring matrix used in Version 11.0 of the GCG Wisconsin Genetics Software Package is BLOSUM62 (see, Henikoff and Henikoff (1989) Proc Natl Acad Sci USA 89:10915).

Unless otherwise stated, percent identity and/or percent similarity values among multiple sequences provided herein refer to the value obtained using ClustalW2 using the following parameters: for nucleotide sequences using gap open of 10, gap extension of 0.2, gap distances of 5, the IUB DNA weight matrix, and the clustering method of Neighbor-joining; for amino acid sequences using gap open of 10, gap extension of 0.2, gap distances of 5, the Gonnet protein weight matrix, and the clustering method of Neighbor-joining.

ClustalW2 is a web-based multiple sequence alignment program for DNA and protein which will generate six result files, including input sequences, tool output, alignment in CLUSTAL format, guide tree, phylogenetic tree, and percent identity matrix. To perform the alignment, in various embodiments, two sets of parameters can be set by users, i.e., pairwise alignment options and multiple sequence alignment options. Parameters selected for pairwise alignment will be used to establish the guided tree for the multiple sequence alignment whereas the latter will calculate the best matches for the input sequences and line them up so that identities, similarities, and differences can be visualized directly.

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. In various embodiments, this involves scoring a conservative substitution as a partial rather than a full mismatch, thereby increasing the percentage sequence identity. Thus, in various embodiments, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.). The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In various embodiments, the disclosed sequences may be introduced into plants to alter levels of a K-domain sequence. In other embodiments, plants may have increased expression levels of a K-domain sequence. In various embodiments, the plants have stably incorporated into their genome at least one heterologous polynucleotide encoding a K-domain polypeptide. In various embodiments, sequences that can be used to increase expression of a K-domain polypeptide include, but are not limited to, the sequence set forth in SEQ ID NO: 1 or variants or fragments thereof. Progeny, variants, and mutants of the regenerated plants are also included within the scope, provided that these parts include the introduced or heterologous polynucleotides disclosed herein.

In various embodiments, the disclosed plants can have an altered phenotype. In some embodiments the altered phenotype includes altered flower organ development, flower numbers, leaf numbers and formation, plant size or combinations thereof, but no negative effect on seed or fruit production per plant. In various embodiments, this thereby results in improved yield by increasing plant density in the field and reducing the plant growing period.

In various embodiments, the plant yield is increased by about 5%, 7%, 8%, 9%, or about 10% to 20% or about 30% to about 50% compared to a control plant.

In some embodiments, an increase in yield is seen as an increase in bushels/acre yield. In various embodiments, yield is increased because of phenotypic changes. In various embodiments, the phenotypic changes include change in flowering time, plant height, flower number or a combination thereof when overexpressing VcK. Depending on the plant species, the phenotypes can vary. In various embodiments, ectopic expression of the VcK shortened plant cycles (e.g. 2-3 weeks) and reduced plant sizes. In various embodiments, ectopic overexpression of the VcK promoted more flowers and branch formation. In still other embodiments, overexpressing the VcK increased the number of flowering buds, reduced the amount of chilling requirement for plant flowering. In some embodiments, yield may be increased because of an increase in seed weight, seed size or seed shape. In other embodiments, yield may be increased because of the number of seed (in pods).

Various transformation techniques for a variety of plant species, including, but not limited to, monocots and dicots may be used. In various embodiments, plants include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

In other embodiments, other plants of interest include grain plants that provide seeds of interest, oil-seed plants, and leguminous plants. Seeds of interest include grain seeds, such as corn, wheat, barley, rice, sorghum, rye, and the like. Oil-seed plants include cotton, soybean, safflower, sunflower, *Brassica*, maize, alfalfa, palm, coconut, and the like. Leguminous plants include beans and peas. Beans include guar, locust bean, fenugreek, soybean, garden beans, cowpea, mungbean, lima bean, fava bean, lentils, chickpea, and the like.

In still other embodiments, plants include fruit-bearing plants such as grape, orange, lemon, grapefruit, avocado, date, peach, cherry, olive, plum, coconut, apple, pear blackberry, blueberry, raspberry, strawberry, pineapple, tomato, cucumber and eggplant plants.

In various embodiments, the disclosed polynucleotides employed in the methods and compositions can be provided in expression cassettes for expression in a plant of interest. In some embodiments, the cassette will include 5' and 3' regulatory sequences operably linked to a polynucleotide. In an embodiment, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. In other cases, the additional gene(s) can be provided on multiple expression cassettes. Such an expression cassette may be provided with a plurality of restriction sites, recombination sites or both for insertion of the K-domain polynucleotide to be under the transcriptional regulation of the regulatory regions. In various embodiments, the expression cassette may additionally contain selectable marker genes. In some embodiments, the expression cassette can include in the 5'-3' direction of transcription, a transcriptional and translational initiation region (e.g., a promoter), a K-domain polynucleotide, and a transcriptional and translational termination region (e.g., termination region) functional in plants. In various embodiments, the regulatory regions (e.g., promoters, transcriptional regulatory regions, and translational termination regions), the K-domain polynucleotide or both may be native/analogous to the host cell or to each other. In other embodiments, the regulatory regions, the K-domain polynucleotides or both may be heterologous to the host cell or to each other. In one embodiment, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. In some embodiments, a chimeric gene having a coding sequence operably linked to a transcription initiation region that is heterologous to the coding sequence. In other embodiments, heterologous promoters or the native promoter sequences may be used to express the sequences. In various embodiments, the termination region may be native with the transcriptional initiation region, may be native with the operably linked K-domain polynucleotide, may be native with the plant host, or may be derived from another source (e.g., foreign or heterologous) to the promoter, the K-domain polynucleotide, the plant host, or any combination thereof. Convenient termination regions are available from the Ti-plasmid of *A. tumefaciens*, such as the octopine synthase and nopaline synthase termination regions. See also, Guerineau, et al., (1991) Mol Gen Genet 262:141-144; Proudfoot (1991) Cell 64:671-674; Sanfacon, et al., (1991) Genes Dev 5:141-149; Mogen, et al., (1990) Plant Cell 2:1261-1272; Munroe, et al., (1990) Gene 91:151-158; Ballas et al., (1989) Nucleic Acids Res 17:7891-7903; and Joshi, et al., (1987) Nucleic Acids Res 15:9627-9639.

Where appropriate, the polynucleotides may be optimized for increased expression in the transformed plant. That is, the polynucleotides can be synthesized using plant-preferred codons for improved expression. See, for example, Campbell and Gown (1990) Plant Physiol 92:1-11 for a discussion of host-preferred codon usage. Methods are available in the art for synthesizing plant-preferred genes. See, for example, U.S. Pat. Nos. 5,380,831 and 5,436,391, and Murray, et al., (1989) Nucleic Acids Res 17:477-498, each herein incorporated by reference.

Additional sequence modifications are known to enhance gene expression in a cellular host. These include elimination of sequences encoding spurious polyadenylation signals, exon-intron splice site signals, transposon repeats, and other such well-characterized sequences that may be deleterious to gene expression. The G-C content of the sequence may be adjusted to levels average for a given cellular host, as calculated by reference to known genes expressed in the host cell. When possible, the sequence may be modified to avoid predicted hairpin secondary mRNA structures.

The expression cassettes may additionally contain 5' leader sequences. Such leader sequences can act to enhance translation. Translation leaders are known in the art and include, for example picornavirus leaders, EMCV leader (Encephalomyocarditis 5' noncoding region) (Elroy-Stein, et al., (1989) Proc Natl Acad Sci USA 86:6126-6130); potyvirus leaders, for example, TEV leader (Tobacco Etch Virus) (Gallie, et al., (1995) Gene 165(2):233-238), MDMV leader (Maize Dwarf Mosaic Virus) (Virology 154:9-20), and human immunoglobulin heavy-chain binding protein (BiP) (Macejak, et al., (1991) Nature 353:90-94); untranslated leader from the coat protein mRNA of alfalfa mosaic virus (AMV RNA 4) (Jobling, et al., (1987) Nature 325:622-625); tobacco mosaic virus leader (TMV) (Gallie, et al., (1989) in Molecular Biology of RNA, ed. Cech (Liss, New York), pp. 237-256); and maize chlorotic mottle virus leader (MCMV) (Lommel, et al., (1991) Virology 81:382-385). See also, Della-Cioppa, et al., (1987) Plant Physiol 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In various embodiments, promoters include the native promoter of the polynucleotide sequence of interest. The promoters can be selected based on the desired outcome. The nucleic acids can be combined with constitutive, tissue-preferred, inducible or other promoters for expression in plants. In some embodiments, constitutive promoters include the core promoter of the Rsyn7 promoter and other constitutive promoters disclosed in WO 99/43838 and U.S. Pat. No. 6,072,050; the core CaMV 35S promoter (Odell, et al., (1985) Nature 313:810-812); rice actin (McElroy, et al., (1990) Plant Cell 2:163-171); ubiquitin (Christensen, et al., (1989) Plant Mol Biol 12:619-632 and Christensen, et al., (1992) Plant Mol Biol 18:675-689); pEMU (Last, et al., (1991) Theor Appl Genet 81:581-588); MAS (Velten, et al., (1984) EMBO J 3:2723-2730); ALS promoter (U.S. Pat. No. 5,659,026), GOS2 promoter (dePater, et al., (1992) Plant J 2:837-44), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

In various embodiments, a tissue-specific promoter is a promoter that is active in transcription in the organs or tissue of roots, stem, leaves, or seeds. For example, a root-specific promoter is a promoter that is active in transcription predominantly in plant roots. Various tissue-specific promoters are disclosed in U.S. Pat. No. 8,697,947.

In various embodiments, the expression cassette can also include a selectable marker gene for the selection of transformed cells. Selectable marker genes may be used for the selection of transformed cells or tissues. In various embodiments, marker genes include genes encoding antibiotic resistance, such as those encoding neomycin phosphotransferase II (NPT II) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). In other embodiments, selectable markers include phenotypic markers such as 13-galactosidase and fluorescent proteins such as green fluorescent protein (GFP) (Su, et al., (2004) Biotechnol Bioeng 85:610-9 and Fetter, et al., (2004) Plant Cell 16:215-28), cyan florescent protein (CYP) (Bolte, et al., (2004) J Cell Science 117:943-54 and Kato, et al., (2002) Plant Physiol 129:913-42), and yellow florescent protein (PhiYFP™ from Evrogen, see, Bolte, et al., (2004) J Cell Science 117:943-54). For additional selectable markers, see generally, Yarranton (1992) Curr Opin Biotech 3:506-511; Christopherson. et al., (1992) Proc Natl. Acad. Sci. USA 89:6314-6318; Yao, et al., (1992) Cell 71:63-72; Reznikoff (1992) Mol Microbiol 6:2419-2422; Barkley, et al., (1980) in The Operon, pp. 177-220; Hu, et al., (1987) Cell 48:555-566; Brown, et al., (1987) Cell 49:603-612; Figge, et al., (1988) Cell 52:713-722; Deuschle, et al., (1989) Proc Natl Acad Aci USA 86:5400-5404; Fuerst, et al., (1989) Proc Natl Acad Sci USA 86:2549-2553; Deuschle, et al., (1990) Science 248:480-483; Gossen (1993) Ph.D. Thesis, University of Heidelberg; Reines, et al., (1993) Proc Natl Acad Sci USA 90:1917-1921; Labow, et al., (1990) Mol Cell Biol 10:3343-3356; Zambretti, et al., (1992) Proc Natl Acad Sci USA 89:3952-3956; Bairn, et al., (1991) Proc Natl Acad Sci USA 88:5072-5076; Wyborski, et al., (1991) Nucleic Acids Res 19:4647-4653; Hillenand-Wissman (1989) Topics Mol Struc Biol 10:143-162; Degenkolb, et al., (1991) Antimicrob Agents Chemother 35:1591-1595; Kleinschnidt, et al., (1988) Biochemistry 27:1094-1104; Bonin (1993) Ph.D. Thesis, University of Heidelberg; Gossen, et al., (1992) Proc Natl Acad Sci USA 89:5547-5551; Oliva, et al., (1992) Antimicrob Agents Chemother 36:913-919; Hlavka, et al., (1985) Handbook of Experimental Pharmacology, Vol. 78 (Springer-Verlag, Berlin); Gill, et al., (1988) Nature 334: 721-724. Such disclosures are herein incorporated by reference. The above list of selectable marker genes is not meant to be limiting. Any selectable marker gene can be used.

In various embodiments, the disclosed polynucleotides can be stacked with any combination of polynucleotide sequences of interest to create plants with a desired trait. In other embodiments, the combinations generated can also include multiple copies of any one of the polynucleotides of interest. In still other embodiments, the disclosed polynucleotides can also be stacked with traits desirable for disease or herbicide resistance (e.g., fumonisin detoxification genes (U.S. Pat. No. 5,792,931); avirulence and disease resistance genes (Jones, et al., (1994) Science 266:789; Martin, et al., (1993) Science 262:1432; Mindrinos, et al., (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) J Bacteriol 170:5837-5847) facilitate expression of polyhydroxyalkanoates (PHAs)); the disclosures of which are herein incorporated by reference. One could also combine the disclosed polynucleotides with polynucleotides providing agronomic traits such as male sterility (e.g., see U.S. Pat. No. 5,583,210), stalk strength, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, in various embodiments the disclosed polynucleotide sequences can be combined at any time and in any order. In some embodiments, a transgenic plant having one or more desired traits can be used as the target to introduce further traits by subsequent transformation. The traits can be introduced simultaneously in a co-transformation protocol with the disclosed polynucleotides provided by any combination of transformation cassettes. In one embodiment, if two sequences will be introduced, the two sequences can be contained in separate transformation cassettes (trans) or contained on the same transformation cassette (cis). Expression of the sequences can be driven by the same promoter or by different promoters. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The various embodiments provide for methods that involve introducing a polynucleotide or polypeptide into a plant. Any suitable method for introducing a sequence into a plant may be used such that the polynucleotide or polypeptides gains access to the interior of at least one plant cell. Methods for introducing polynucleotide or polypeptides into plants are known in the art including, but not limited to, stable transformation methods, transient transformation methods, and virus-mediated methods.

Transformation protocols as well as protocols for introducing polypeptides or polynucleotide sequences into plants may vary depending on the type of plant or plant cell, e.g., monocot or dicot, targeted for transformation. Suitable methods of introducing polypeptides and polynucleotides into plant cells include microinjection (Crossway, et al., (1986) Biotechniques 4:320-334), electroporation (Riggs, et al., (1986) Proc Natl Acad Sci USA 83:5602-5606, *Agrobacterium*-mediated transformation (U.S. Pat. Nos. 5,563, 055 and 5,981,840), direct gene transfer (Paszkowski, et al., (1984) EMBO J 3:2717-2722), and ballistic particle acceleration (see, for example, U.S. Pat. Nos. 4,945,050; 5,879,918; 5,886,244; and U.S. Pat. No. 5,932,782; Tomes, et al., (1995) in Plant Cell, Tissue, and Organ Culture: Fundamental Methods, ed. Gamborg and Phillips (Springer-Verlag, Berlin); McCabe, et al., (1988) Biotechnology 6:923-926); and Led transformation (WO 00/28058). Also see, Weissinger, et al., (1988) Ann Rev Genet 22:421-477; Sanford, et al., (1987) Particulate Science and Technology 5:27-37 (onion); Christou, et al., (1988) Plant Physiol 87:671-674 (soybean); McCabe, et al., (1988) Bio/Technology 6:923-926 (soybean); Finer and McMullen (1991) In Vitro Cell Dev Biol 27P:175-182 (soybean); Singh, et al., (1998) Theor Appl Genet 96:319-324 (soybean); Datta, et al., (1990) Biotechnology 8:736-740 (rice); Klein, et al., (1988) Proc Natl Acad Sci USA 85:4305-4309 (maize); Klein, et al., (1988) Biotechnology 6:559-563 (maize); U.S. Pat. Nos. 5,240,855; 5,322,783; and U.S. Pat. No. 5,324,646; Klein, et al., (1988) Plant Physiol 91:440-444 (maize); Fromm, et al., (1990) Biotechnology 8:833-839 (maize); Hooykaas-Van Slogteren, et al., (1984) Nature (London) 311:763-764; U.S. Pat. No. 5,736,369 (cereals); Bytebier, et al., (1987) Proc Natl Acad Sci USA 84:5345-5349 (Liliaceae); De Wet, et al., (1985) in The Experimental Manipulation of Ovule Tissues, ed. Chapman, et al., (Longman, N.Y.), pp. 197-209 (pollen); Kaeppler, et al., (1990) Plant Cell Reports 9:415-418 and Kaeppler, et al., (1992) Theor Appl Genet 84:560-566 (whisker-mediated transformation); D'Halluin, et al., (1992) Plant Cell 4:1495-1505 (electroporation); Li, et al., (1993) Plant Cell Reports 12:250-255 and Christou and Ford (1995) Annals of Botany 75:407-413 (rice); Osjoda, et al., (1996) Nature Biotechnology 14:745-750 (maize via *Agrobacterium tumefaciens*); all of which are herein incorporated by reference.

In some embodiments, the K-domain sequences or variants thereof can be provided to a plant using a variety of transient transformation methods. Such transient transformation methods include, but are not limited to, the introduction of the K-domain or variants thereof directly into the plant or the introduction of the K-domain transcript into the plant. Such methods include, for example, microinjection or particle bombardment. See, for example, Crossway, et al., (1986) Mol Gen Genet 202:179-185; Nomura, et al., (1986) Plant Sci 44:53-58; Hepler, et al., (1994) Proc Natl Acad Sci 91:2176-2180 and Hush, et al., (1994) The Journal of Cell Science 107:775-784, all of which are herein incorporated by reference. Other techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (e.g., PEI; Sigma #P3143).

In other embodiments, the polynucleotide may be introduced into plants by contacting plants with a virus or viral nucleic acids. In some embodiments, such methods involve incorporating a nucleotide construct within a viral DNA or RNA molecule. In one embodiment the K-domain sequence or a variant thereof may be initially synthesized as part of a viral polyprotein, which later may be processed by proteolysis in vivo or in vitro to produce the desired recombinant protein. In various embodiments, the promoters also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta, et al., (1996) Molecular Biotechnology 5:209-221; herein incorporated by reference.

A variety of methods for the targeted polynucleotide insertion at a specific location in the plant genome may be used. In some embodiments, the polynucleotide insertion at a desired genomic location is achieved using a site-specific recombination system. See, for example, WO99/25821, WO99/25854, WO99/25840, WO99/25855, and WO99/25853, all of which are herein incorporated by reference. In one embodiment, the disclosed polynucleotide can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The disclosed polynucleotide is thereby integrated at a specific chromosomal position in the plant genome.

The cells that have been transformed may be grown into plants in accordance with conventional ways. See, for example, McCormick, et al., (1986) Plant Cell Reports 5:81-84. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, in one embodiment, transformed seed (also referred to as "transgenic seed") having a polynucleotide, stably incorporated into their genome may be made. In other embodiments, transformed seed or transgenic seed have an expression cassette stably incorporated into their genome.

Any method or composition that modulates expression of a target gene product (e.g., overexpression or knock-down expression), either at the level of transcription or translation, or modulates the activity of the target gene product can be used to achieve overexpression, concentration, activation of the target gene product. In various embodiments, the level is increased by at least 1%, 5%, 10%, 20%, 30%, 40%, 50%, 60%, 70%, 80%, 90% or greater including any range or value there between relative to an appropriate control plant, plant part, or cell. Expression may occur during, subsequent to plant growth at a desired development stage or both. In some embodiments, the disclosed polypeptides are modulated in fruit bearing plants. In other embodiments, the fruit bearing plants include blueberries and the like.

In various embodiments, the expression level of a polypeptide having a K domain or a biologically active variant or fragment thereof may be measured directly or indirectly. In some embodiments, the expression level of a polypeptide having a K domain or a biologically active variant or fragment thereof may be measured by assaying for the level of the K-domain polypeptide in the plant.

In other embodiments, the expression level of a polypeptide having a K domain or a biologically active variant or fragment thereof may be measured by measuring the level of the polynucleotide encoding the protein or by measuring the activity of the K-domain polypeptide in the plant. The polypeptide or the polynucleotide may be introduced into a plant cell. The plant cell having the introduced sequence may be selected using methods known to those of skill in the art such as, but not limited to, Southern blot analysis, Northern blot, DNA sequencing, PCR analysis, or phenotypic analysis. In various embodiments, a plant or plant part altered or modified by the foregoing may be grown under plant-promoting conditions for a time sufficient to modulate the concentration and/or activity of disclosed polypeptides in the plant.

In various embodiments, the level and/or activity of the polypeptide may be modulated by employing a polynucleotide that is not capable of directing, in a transformed plant, the expression of a protein or an RNA. For example, the polynucleotide may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham, et al., (1999) Proc Natl Acad Sci USA 96:8774-8778; herein incorporated by reference.

The various methods described herein do not depend on the incorporation of the entire polynucleotide into the genome, only that the plant or cell thereof may be altered as a result of the introduction of the polynucleotide into a cell. In various embodiments, the genome may be altered following the introduction of the polynucleotide into a cell. In other embodiments, the polynucleotide, or any part thereof, may incorporate into the genome of the plant. Alterations to the genome include, but are not limited to, additions, deletions, and substitutions of nucleotides into the genome.

The activity, level or both of a K-domain polypeptide is increased. In various embodiments, an increase in the activity, level or both of the K-domain polypeptide is by providing to the plant a K-domain polypeptide or a biologically active variant or fragment thereof. As discussed elsewhere herein, many methods are known in the art for providing a polypeptide to a plant including, but not limited to, direct introduction of the K-domain polypeptide into the plant or introducing into the plant (transiently or stably) a polynucleotide construct encoding a polypeptide having K-domain activity. In various embodiments, the level and/or activity of a K-domain polypeptide may be increased by altering the gene encoding the K-domain polypeptide or its promoter. See, e.g., Kmiec, U.S. Pat. No. 5,565,350; Zarling, et al., PCT/US93/03868. Therefore, mutagenized plants that carry mutations in K-domain genes, where the mutations increase expression of the K-domain gene or increase the activity of the encoded K-domain polypeptide, are provided.

In various embodiments, the level of a single K-domain sequence can be modulated to produce the desired phenotype. In other embodiments, the level of expression of multiple sequences having a K-domain or a biologically active variant or fragment thereof are modulated. In still other embodiments, the level of the K-domain sequence is modulated by an increase.

The various embodiments will be further described by reference to the following examples, which are offered to further illustrate various embodiments. It should be understood, however, that many variations and modifications may be made while remaining within the scope of the various embodiments.

Example 1

Materials and Methods
Cloning and Phylogenetic Analysis of VcK-Domain

To generate cDNA sequences for cloning of VcK-domain, total RNA was isolated from vernalized flower buds from a northern highbush blueberry (*Vaccinium corymbosum* L.) cultivar, Bluecrop, using the RNeasy Plant Mini Kit (Qiagen, Valencia, Calif., USA) with modifications as described by Dhanaraj et al. (2004). Following isolation, the sample was treated with RQ1 DNase (Promega, Madison, Wis., USA) according to the manufacturer's instructions, followed by chloroform:isoamyl alcohol (24:1) extraction, 100% ethanol precipitation, 70% ethanol wash, and finally resuspended in diethylpyrocarbonate (DEPC)-treated water. Total RNA (0.6 µg) was reverse transcribed into complementary DNA (cDNA) using SuperScript II Reverse Transcriptase (Invitrogen, Carlsbad, Calif., USA). One-tenth of the cDNA was used in one PCR amplification reaction using GoTaq Green Master Mix (Promega).

Blueberry EST sequence "*Vaccinium_corymbosum*_v1_Contig03391", downloaded from the blueberry EST database was used to design primers for VcK-domain. Nested PCRs were conducted using primers SOCF1 and SOCR1 for the $1^{st}$ round of amplification and SOF1 and SOK (see Table 1) for the $2^{nd}$ round of amplification. PCR products were cloned into a pCR 2.1-TOPO vector (Invitrogen) and verified by sequencing.

TABLE 1

Primers used.

| Primer name | Sequence | Target |
|---|---|---|
| SOCF1 | SEQ ID NO: 4 | Blueberry SUPPRESSOR |
| SOCR1 | SEQ ID NO: 5 | OF OVEREXPRESSION |
| SOF1: | SEQ ID NO: 6 | OF CONSTANS 1-like gene (VcK-domain) |
| SOK: | SEQ ID NO: 7 | |
| 35S-F | SEQ ID NO: 8 | 3' portion of the CaMV 35S promoter |
| NPTII-F | SEQ ID NO: 9 | Neomycin phosphotransferase II gene |
| NPTII-R | SEQ ID NO: 10 | (nptII) |
| Actin-F | SEQ ID NO: 11 | Actin |
| Actin-R | SEQ ID NO: 12 | |
| BBK-domain - F | SEQ ID NO: 13 | VcK-domain |
| BBK-domain - R | SEQ ID NO: 14 | |

Amino acid and nucleotide sequences of VcK-domain orthologues were retrieved from the NCBI. Selected amino acid sequences were aligned using the ClustalW2 multiple sequence alignment program (Thompson et al. 1994) at the EBI with default parameters (Protein Weight Matrix: Gonnet, gap open penalty of 10 and gap extension penalty of 0.20, gaps that are closer than 5 amino acids are penalized, clustering method of Neighbour-joining. Phylogenetic analysis of nucleotide sequences of K-domain-like genes from 17 dicot plants and one monocot plant (*Oryza sativa*) by Maximum Likelihood method based on the Tamura-Nei model using the MEGA 5 program (Tamura et al. 2011) was performed. OsMADS56 was used as an outgroup and the black dot denotes the K-domain-like protein from blueberry (VcK-domain-like). Rate variation among sites was modeled using a discrete Gamma distribution (4 categories) with invariant sites (G+I). The tree was drawn to scale, with the branch length equal to the number of substitutions per nucleotide.

Construction of the Expression Vector and Transformation of Tobacco

To make a construct for plant transformation, the 5'-XbaI-VcK-domain-SacI-3' fragment was released from the pCR2.1-TOPO vector and then inserted into the opened XbaI and SacI sites in the T-DNA region between the cauliflower mosaic virus (CaMV) 35S promoter and the Nos terminator in pBI121, where the GUS (β-glucuronidase) coding region was removed. The resulting 35S-VcK-domain was sequenced to confirm the VcK-domain sequence and subsequently introduced into *Agrobacterium tumefaciens* strain EHA105 (Hood et al. 1993) using the freeze-thaw method.

*Agrobacterium*-mediated transformation of tobacco (*Nicotiana tabacum* L. cv Samsun) leaf explants with 35S-VcK-domain was conducted according to Horsch et al. (1985). Kanamycin-resistant shoots were rooted on Murashige and Skoog medium (MS) (1962) containing 100 mg $L^{-1}$ kanamycin monosulfate (Km). Transgenic plants from separate leaf explants were considered as independent transgenic events.

To confirm the presence of the transgene, DNA was isolated from leaf tissues using a cetyltrimethylammonium bromide (CTAB) method (Doyle and Doyle, 1987). Two pairs of primers (Table 1) were used for PCR verification: nptII-F and nptII-R for the nptII gene, and 35S-F (3' portion of the CaMV 35S promoter) and SOK for the VcK-domain gene.

Reverse-Transcription PCR (RT-PCR) Analyses

Total RNA was isolated from young leaves of selected T0 tobacco plants using an RNeasy Plant Mini Kit (Qiagen, Valencia, Calif., USA) with on-column RNase-free DNase (Qiagen) treatment according to the manufacturer's instructions. Reverse-transcription of RNA to cDNA was carried out using SuperScript II reverse transcriptase (Invitrogen).

The resulting cDNA, 2 µl/sample, was used for PCR amplification of a 160 base pair endogenous actin gene and a 474-base pair fragment of the VcK-domain. The primers are shown in table 1. The reaction conditions for all primer pairs were 94° C. for 2 min, 35 cycles of 45 sec at 94° C., 60 sec at 58° C. and 90 sec at 72° C., with a final 10 min extension at 72° C. All amplified PCR and RT-PCR products were separated on 1.0% agarose gel containing ethidium bromide, visualized and photographed under UV light.

Phenotyping of Transgenic Tobacco Plants

When T0 putative transformants and nontransgenic/control plants grew to the stage of 3-5 leaves, they were transplanted from the MS medium to 10×10 cm pots containing Suremix potting media (Michigan Grower Products Inc, Galesburg, Mich., USA) and grown under a 16-hour photoperiod with 30 µmol $m^{-2}s^{-1}$ light from cool white fluorescent tubes for 3 weeks before being repotted into 1-gallon pots. Flower structure of transgenic plants was compared with control plants through a dissecting microscope. These T0 transgenic plants were self-pollinated to obtain the T1 seeds used in the remainder of the study.

Transgenic tobacco plants with pBI121 (the backbone vector) showed no significant difference in phenotype (e.g., flowering time, plant height, and seed yield) compared to wild type plants. T1 seeds and nontransgenic tobacco were planted in 48-cell trays containing Suremix potting media and maintained under a 16-hour photoperiod with 30 µmol $m^{-2}s^{-1}$ light from cool white fluorescent tubes while transgene presence was confirmed by PCR using 35S-F (SEQ ID NO: 8) and SOK (SEQ ID NO: 7) primers (Table 1). Seedlings of similar size (10 for each transgenic event or control) were then transplanted into 10×10 cm pots and grown in the greenhouse under natural photoperiod (an average of 14.9 hrs of natural sunlight per day) with a minimum temperature of 23° C. in a completely randomized design with regular irrigation and fertilization.

Days to flowering (days between sowing and appearance of the first flower bud), leaf number, plant height, and number of seed pods were recorded for the T1 plants. The number of leaves on the central stem and plant height (from soil level to the bottom of the central flower cluster) were determined when 50% of flowers in the central cluster were open. Number of seed pods in the central flower cluster was determined when plants finished blooming. Statistical analysis was conducted with PROC GLM in SAS 9.3 (SAS Institute Inc., Cary, N.C., USA). Difference from wild type tobacco was determined using Dunnett's two-tailed test ($\alpha$=0.05).

Isolation and Sequence Analysis of VcK-Domain

To search for a K-domain-like gene in blueberry, a *Vitis vinifera* K-domain-like gene (GenBank accession GU133633.1) was used as the query to BLAST against the blueberry EST database. Based on E-value, the top hit was an 1189-bp EST sequence (*Vaccinium_corymbosum*_v1_Contig03391), which contains a MADS-box motif and a K domain. Comparison with K-domain-like genes from other plant species indicates that the Contig03391 contains the full sequence of a blueberry K-domain-like gene (VcK-domain) and is grouped in the clade of K-domain-like genes along with MADS1 (*Nicotiana tabacum*) and MADS8 (*Vitis vinfera*) based on phylogentic analysis (FIG. 1A).

To investigate the function of the K-domain in a SOC1 gene, the K-domain of the VcK-domain, a 471-bp ORF encoding 157 amino acids was cloned. The cloned VcK-domain has three nucleotide mismatches (e.g., positions 51, 171, and 178) from that of the Contig03391. One mismatch resulted in an amino acid substitution. Multiple sequence alignment of nine selected amino acid sequences (e.g., six from woody plants and one from *Arabidopsis*) of VcK-domain orthologues indicates that the VcK-domain is highly conserved in these plant species (FIG. 1B).

Molecular Evidence of the Overexpression of VcK-Domain

RT-PCR confirmed transcription of the VcK-domain (FIG. 2). In young leaves of both transgenic (selected T0) and non-transgenic (NT) plants, the consistent bands of an endogenous actin gene were observed; in contrast, an expected 474-bp fragment of the VcK-domain was observed in all of the transgenic plants tested but was absent in non-transformed plants (FIG. 2). FIG. 2 shows the following lanes; Lanes 1 & 5: transgenic event 15-4; Lanes 2 & 6: transgenic event 15-6; Lanes 3 & 7: NT; Lanes 4 & 8: water as template; and lane M: 1-kb DNA ladder.

Phenotype Changes of VcK-Domain Transgenic Tobacco Plants

Figure 3A:
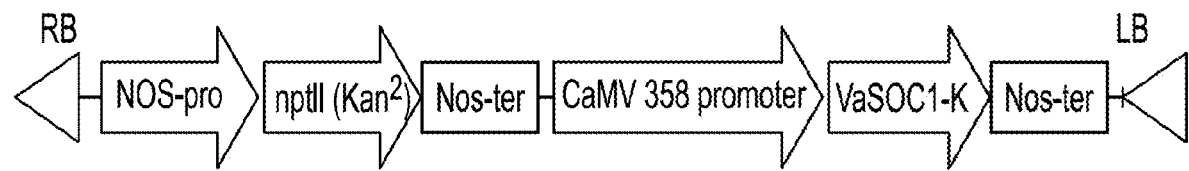
FIG. 3A is a schematic illustration of the T-DNA region carrying the 35S-VcK-domain according to an embodiment.
Figure 3B:
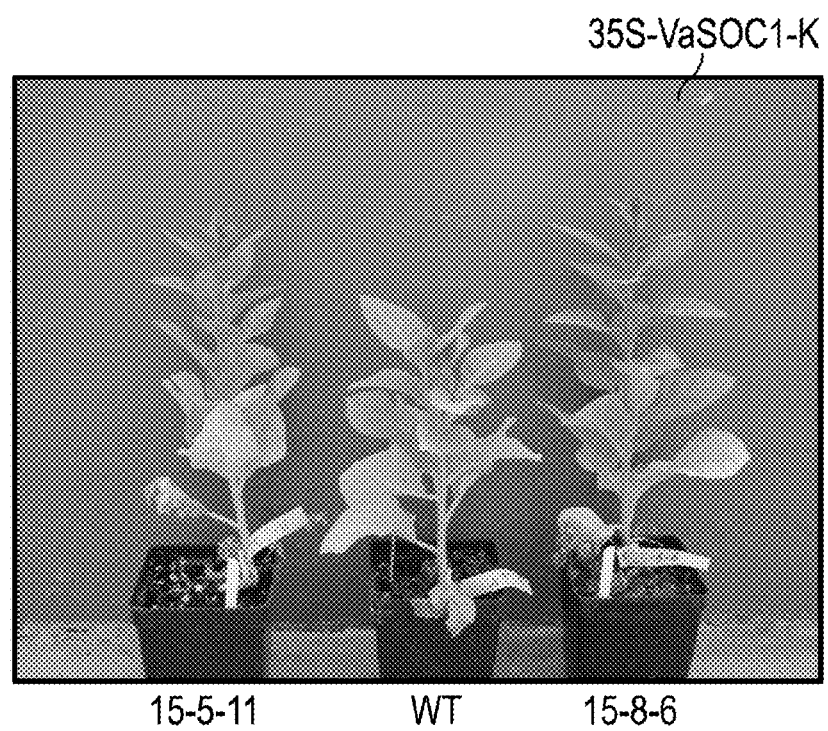
FIG. 3B is a digital image of $T_1$ transgenic plants compared with a nontransgenic wild type (WT) plant 93 days after seed germination according to an embodiment.

Ectopic expression of VcK-domain did not result in any morphological changes in floral organ identity, but promoted early flowering in transgenic tobacco plants (FIG. 3A-C). Of the 22 T0 transgenic events regenerated, all had normal flowers, as did T1 plants derived from five events (I5-5, I5-8, I5-16, I5-18, and I5-22) chosen for continued study. The T1 plants from four of these selected events flowered an average of 18 days (ranging from 15 to 21 days, depending on event) earlier than wild type plants, which flowered 129 days after sowing (FIG. 3B, C). The result suggests that VcK-domain is involved in flower timing.

Although no obvious morphological changes were observed in flowers, VcK-domain transgenic plants did exhibit altered growth. All four early flowering T1 transgenic events showed significant decreases in plant height and one had significantly fewer leaves at the time of flowering compared to wild type plants (FIG. 3D-F).

Expression of 35S-VcK-domain did not significantly affect the number of seed pods in five lines of T1 plants evaluated (P=0.0501), suggesting that expression of the 35S-V cK-domain has little impact on seed or fruit production per plant.

Seed production of 20 T0 plants was compared with non-transgenic plants. The average seed production for 20 transgenic events was 8.02 grams, which is 32% higher than wild type plants (6.08 g/plant), although there is no statistical difference between transgenic plants and wild type plants due to the variations among different transgenic events (Table 2).

TABLE 2

Seed production of transgenic tobacco plants overexpressing the VcK domain

|  | Average seed production per plant (gram) ± STDEV |
|---|---|
| T0 plants of 20 transgenic events | 8.02 ± 2.71 a |
| Three wild type plants | 6.08 ± 0.42 a |

Of the 20 independent transgenic events of tobacco plants, seed yields of 14 events (70%) were higher than the wild type plant. The results suggest a high potential (more than 70% chances) of obtaining individual transgenic events with an increased seed production.

Example 2

Cloning the Full Length VcSOC1 Homologues

Following the protocols for the VcK cloning as described in Example 1, primers BOC-FX (5'-tctagaATGGT-GAGAGGGAAAACCCAGA-3': SEQ ID NO: 15) and BOC-RS (5'-gagctcACTTGGGTGGCGAAACT-3'; SEQ ID NO: 16) were used for amplification of VcSOC1 homologues from cDNA of blueberry cultivar Bluecrop. PCR products were cloned into a pCR2.1-TOPO vector (Invitrogen) and verified by sequencing. Three VcSOC1 homologues were identified as VcSOC1A (SEQ ID NO: 17), VcSOC1B (SEQ ID NO: 18) and VcSOC1D (SEQ ID NO: 19). The 5'-Xba I-VcSOC1-Sac I-3' fragments were released from the pCR2.1-TOPO vectors and then inserted into the opened XbaI and SacI sites in the T-DNA region between the cauliflower mosaic virus (CaMV) 35S promoter and the Nos terminator in pBI121, where the GUS (β-glucuronidase) coding region was removed. The resulting vectors were independently introduced into *Agrobacterium tumefaciens* strain EHA105 and as described in Example 1. Independent transformation of the three VcSOC1 homologues into tobacco was carried out following the protocols for the VcK-domain transformation as described in Example 1.

Molecular Analyses

To evaluate the expression of the three VcSOC1 homologues in tobacco, the SOF1 and SOK primer pair (as shown in Table 1) were used for reverse-transcription PCR (RT-PCR) analyses of T0 plants. The RT-PCR analysis was conducted as described in Example 1.

Phenotyping of Transgenic Tobacco Plants

Phenotyping of transgenic tobacco plants transformed with the three VcSOC1 homologues was conducted in the greenhouse under natural light conditions in the Fall of Michigan. Three T0 transgenic events for each of the VcSOC1 homologues were used. These plants were all RT-PCR positive for the VcSOC1. Each event was proliferated to obtain three plants by in vitro culturing internode cuttings on MS medium; non-transgenic plants and one T1 VcK-domain plant were used as control. These plants were grown in 10×10 cm pots. Days to flowering (days between sowing and appearance of the first flower bud), leaf number, plant height, and number of seed pods were recorded. Ectopic overexpression was determined by the presence of a 657 base pair for VcSOC1A, 576 base pair for VcSOC1B, and 654 base pair VcSOC1D.

Ectopic overexpression of the three VcSOC1 homologues (VcSOC1A, VcSOC1B, and VcSOC1D) showed similar function as overexpression of the VcK-domain, such as early flowing (1-3 week earlier than non-transgenic controls) without significantly reducing the leaf number and the number of seed pots per T0 transgenic tobacco plant.

Example 3

The VcK-domain construct as described in Example 1 was used to ectopically overexpress the VcK in blueberry plants. To this end, transformation of a northern highbush blueberry cultivar Aurora was performed as reported in Song and Sink, (*Agrobacterium tumefaciens*-mediated transformation of blueberry (*Vaccinium corymbosum* L.). Plant Cell Rep. 23: 475-484 and Song G-Q, Sink KC (2006) *Agrobacterium*-mediated transformation of highbush blueberry (*Vaccinium corymbosum* L.) cultivars. In: Wang K, ed. *Agrobacterium protocols: Methods in molecular biology* 344. 2nd edn. Totowa N.J.: Humana Press, 37-44. Briefly, leaf explants were co-cultivated with EHA105 for 6 days on co-cultivation medium in the presence of 100 µM acetosyringone at 25° C. in the dark. Selection and regeneration was carried out on regeneration medium (modified McCown's Woody Plant Medium (WPM) containing 4.54 µM thidiazuron, 2.69 µM α-naphthaleneacetic acid, 10 mg L$^{-1}$ Km, and 250 mg L$^{-1}$ cefotaxime) for 12 weeks. Subcultures to fresh selection medium were conducted at four-week intervals. Transgenic shoots from separate explants were used as independent transgenic events. Proliferation of individual kanamycin-resistant shoots was conducted on WPM containing 4.56 µM zeatin, 50 mg L$^{-1}$ Km, and 250 mg L$^{-1}$ cefotaxime. Wild type controls were regenerated from non-infected leaf explants and transgenic controls were transformated with a gusA gene instead of the 35S-VcK construct.

Six plants for each of the three T0 transgenic events transformed with the VcK were obtained through micro-propagation and they were grown in 3.78-L [17.78 cm (height)×20.32 cm (diameter)] pots in the greenhouse under natural light conditions. Non-transgenic plants and transgenic plants transformed with pBI121 were used as controls. Plant height, number of branches, number of flowering buds, and date of flowering were recorded.

Transgenic plants showed accelerated flowering and flowered under no-chilling conditions, where non-transgenic plants did not flower. This suggests overexpressing the VcK-domain is sufficient to promote accelerated blueberry flowering.

Example 4

The VcK-domain construct as described in Example 1 was used to ectopically overexpress the VcK in *petunia* plants. *Agrobacterium*-mediated transformation of *Petunia hybrida* Mitchell was performed essentially as described by Jorgensen et al. (1996). Briefly, leaf explants, 2-3×2-4 mm, were excised from in vitro seedlings grown on half-strength MS basal medium (Murashige and Skoog 1962). Co-cultivation was carried out for 4 days on regeneration medium (RM: MS+4.4 1 M BAP+1.1 1 M IAA) supplemented with 100 1 M acetosyringone. Following selection with 250 mg $l^{-1}$ Timentin and 100 mg 1 kanamycin, transgenic shoots were produced on RM and rooted on MS. The cultures were maintained at 25° C. under a 16-h light photoperiod. Empty vector (pGA643) and non-transformed explants were also carried through tissue culture as negative controls. T1 seeds were harvested from separate T0 plants.

Phenotyping of *petunia* plants was performed between January and June in the greenhouse under natural light conditions in Michigan. Fifteen T1 seedlings of two independent events transformed with the VcK were grown in 10×10 cm pots. VcK presence in transgenic seedlings was confirmed by PCR using 35S-F (SEQ ID NO: 8) and SOK (SEQ ID NO: 7) primers (Table 1). Fifteen plants for each non-transgenic and transgenic seedlings transformed with pGA643, were used as controls. Days to flowering (days between sowing and appearance of the first flower bud), number of flowers, branches and height of the central stem were recorded. (Table 3)

TABLE 3

Effect of ectopic expression of 35S:VcK on phenotypic changes in $T_1$ transgenic *petunia* plants

| Plant | Days to emergence of first flowers after the seeds were sown | Number of plant branches per plant (investigated on Jun. 23$^{th}$, 2014) | Number of total flowers per plant (investigated on Jun. 23$^{th}$, 2014) |
|---|---|---|---|
| $T_1$ transgenic plants overexpressing VcK | 74 | 5.1 | 76.4 |
| Wild-type | 83 | 2.6 | 48.2 |
| $T_1$ transgenic control plants transformed with pGA643 | 82 | 2.5 | 48.3 |

Compared to wild-type *Petunia hybrida* Mitchell and transgenic control plants containing pGA643, VcK overexpressing *petunia* plants flowered 3-9 days earlier, had more branches and more flowers per plant. These transgenic plants also did not show a significant decrease in plant height and the leaf number on the central stem.

Example 5

Figure 3G:
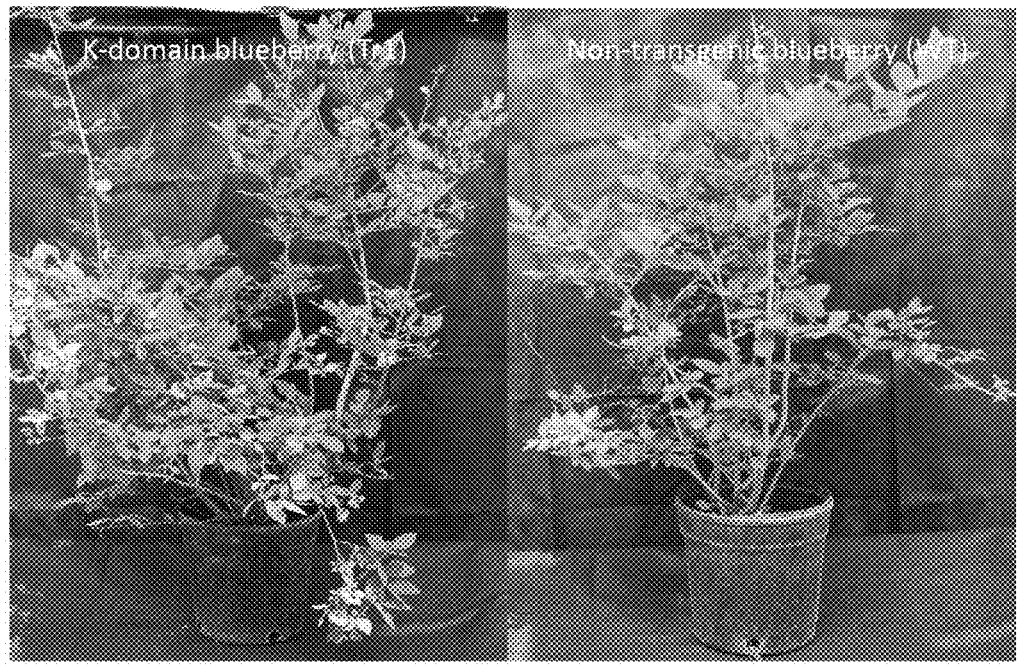
FIG. 3G is a digital image of a 4-year old transgenic (Tr1: containing 35S-VcK-domain) with nontransgenic blueberry (WT) plants in berry production.
Figure 3H:
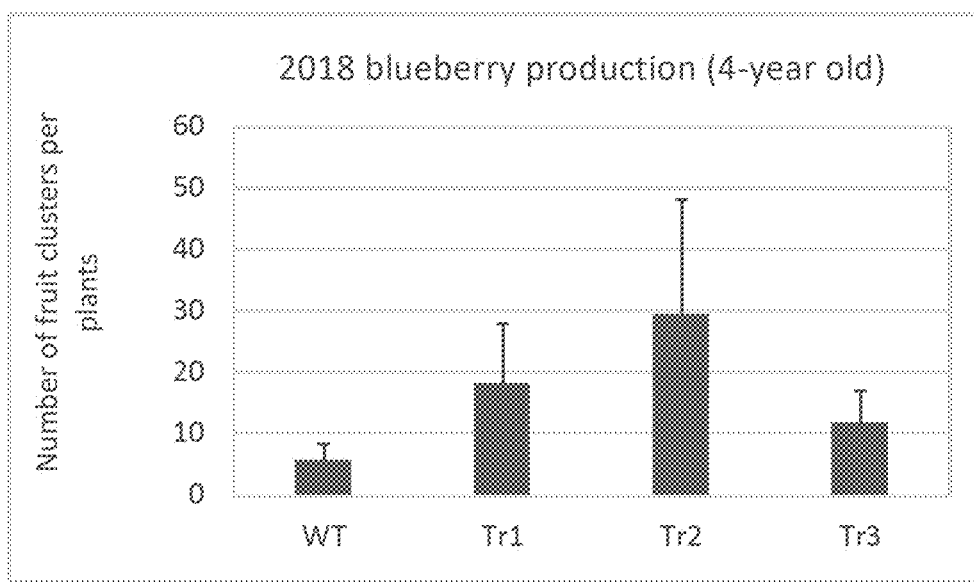
FIG. 3H is a graph showing berry productions in transgenic (Tr1-Tr3: independent transgenic lines containing 35S-VcK-domain) and nontransgenic blueberry (WT) plants.

The VcK-domain construct as described in Example 1 was used to overexpress the VcK in blueberry cultivar Aurora plants. The northern highbush blueberry cultivar Aurora needs more than 1,000 chilling units to induce normal flowering. Transgenic 'Aurora' plants of three independent transgenic events (namely Tr1, Tr2, and Tr3) were obtained using *Agrobacterium tumefaciens*-mediated transformation as described in Song GQ. 2015. (Blueberry (*Vaccinium corymbosum* L.). In *Agrobacterium* Protocols (3$^{rd}$ Edition)-Methods in Molecular Biology 1224 (Wang K. et al. eds.), Humana, Totowa, N.J. Page 121-132). Stable transformation was confirmed using Southern blot analysis of the nptII gene and the whole genome sequencing data, and stable expression of nptII was verified by reverse transcriptase PCR (RT-PCR) and RNA sequencing. Four-year old nontransgenic 'Aurora' (WT) and transgenic plants of three transgenic events (i.e., Tr1, Tr2, and Tr3) were grown for phenotyping (Song and Chen, 2018 Overexpression of the MADS-box gene K-domain increases the yield potential of blueberry. *Plant Science*. 276: 22-31). FIG. 3G is a digital image of a 4-year old transgenic (Tr1: containing 35S-VcK-domain) with nontransgenic blueberry (WT) plants in berry production. FIG. 3H is a graph showing berry productions in transgenic (Tr1-Tr3: independent transgenic lines containing 35S-VcK-domain) and nontransgenic blueberry (WT) plants.

Example 6

Figure 4A:
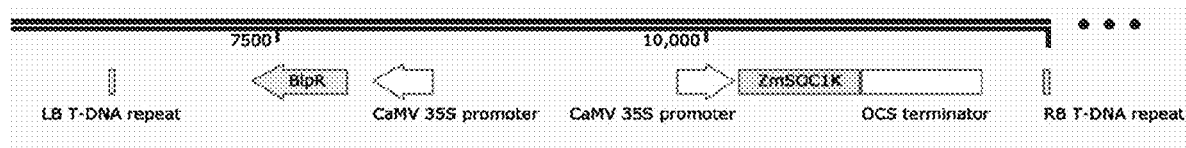
FIG. 4A is a schematic illustration of the T-DNA region carrying the Zm-SOC1K-domain according to an embodiment.

The maize (*Zea mays*) SOC1-K domain from inbred maize 'B107' was constructed using procedures described in the Examples above. The DNA sequence of the maize K-domain is described in SEQUENCE ID NO: 29 and the amino acid sequence is described in SEQUENCE ID NO: 30. Briefly, the maize K-domain construct is driven by the CaMV 35S promoter (a strong constitutive promoter) and the OCS terminator. The Bar gene conferring herbicide resistance to bialophos or phosphinothricin was the selectable marker. (See FIG. 4A) The maize SOC1-K domain construct was used to overexpress the maize SOC1-K domain in maize plants. To this end, transformation of maize 'Hi-II (A188×B73)' was performed using *Agrobacterium tumefaciens* mediated transformation. Embryogenic calluses induced from immature embryos of the 'Hi-II' were used for inoculation with *Agrobacterium tumefaciens* containing the maize K-domain construct. Herbicide-resistant transgenic plants ($T_0$) were produced after selection.

The $T_0$ plants were pollinated using 'B73' pollen to produce $T_1$ transgenic seeds as well as $T_1$ nontransgenic seeds from the same cross.

The $T_0$ transgenic plants were Hi-II (A188×B73) with 50% having B73 background. The $T_1$ transgenic plants were from the seeds of $T_0$ transgenic plants backcrossed with B73 and having 75% B73 background. The $T_1$ nontransgenic (NT) plants were from the seeds of $T_0$ transgenic plants backcrossed with B73 and having 75% B73 background.

Plants were phenotyped and the $T_1$ transgenic plants and $T_1$ NT plants were compared. The results of overexpression of the maize SOC1-K domain are shown in FIGS. 4B-4F. FIG. 4B is a photograph of the $T_1$ transgenic plants. The arrows in the photograph indicate the transgenic plants.

The major phenotypic changes include flowering time, plant height, harvest time, ear weight, and cob weight. FIGS. 4C-4F indicate that tassel appearance, plant height, yield and plant growth rate are increased in the transgenic maize plants.

FIG. 4B is a digital image of $T_1$ transgenic plants compared with a nontransgenic wild-type (WT) plant 102 days after seed sown according to an embodiment. FIG. 4C is a graph showing days to emergence of first flowers after the seeds were sown. FIG. 4D is a graph showing height (cm) from soil to first corn after the seeds were sown. FIG. 4E is a graph showing yield. FIG. 4F is a graph showing plant height (cm) after the seeds were sown.

In maize, the overexpression of maize SOC1-K-domain resulted in fast-growing of the maize plants and an estimate of 10-25% increase of the yields.

Example 7

The soybean (*Glycine max*) K-domain of a MIKC protein of the SUPPRESSOR OF OVEREXPRESSION OF CONSTANS 1 (SOC1) gene (GmSOC1K) has been cloned. The SOC1-K domain is from inbred soybean cultivar Thorne. The DNA sequence of the soybean K-domain is described in SEQUENCE ID NO: 33 and the amino acid sequence is described in SEQUENCE ID NO: 34.

Figure 5A:
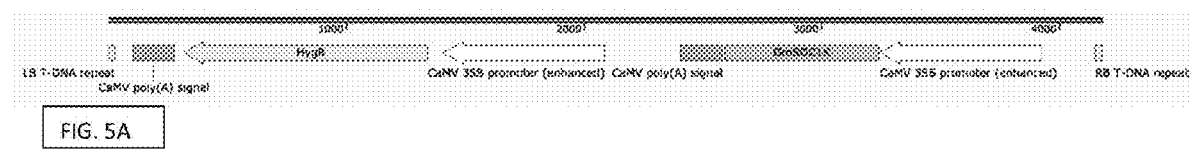
FIG. 5A is a schematic illustration of the T-DNA region carrying the Gm-SOC1K-domain according to an embodiment.

Briefly, the soybean K-domain construct is driven by the CaMV 35S promoter (a strong constitutive promoter) and the CaMV terminator. The hph gene conferring hygromycin resistance is the selectable marker. (See FIG. 5A)

The soybean SOC1-K domain construct was used to ectopically overexpress the soybean SOC1-K domain in tomato plants. To this end, transformation of the tomato plants was performed using *Agrobacterium tumefaciens* mediated transformation. Cotyledons of tomato cultivar Alisa Craig were inoculated with *Agrobacterium tumefaciens* containing the soybean SOC1-K domain. Transgenic $T_0$ plants were selected using 10 mg/L hygromycin.

The $T_0$ transgenic plants are tomato cultivar Alisa Craig. The $T_0$ transgenic plants (TR) are from the inoculated cotyledon explants. The $T_0$ nontransgenic (NT) plants are from uninoculated cotyledon explants.

The transgenic and the non-transgenic plants were compared. Phenotype analysis for 13 comparable TR (from GmSOC1K-1 to GmSOC1K-13) and eight NT plants (from NT1 to NT8) were compared.

Figure 5B:
FIG. 5B is a digital image of $T_0$ transgenic plants compared with a nontransgenic wild type (WT) plant 52 days after the in vitro plants were transplanted to soil according to an embodiment.

Major phenotypic changes were seen in flowering time, plant height, the number of flower clusters, the time of the appearance of the first mature fruit, fruit number, and fruit weight per plant. FIG. 5B is a digital image of $T_0$ transgenic plants compared with a nontransgenic wild type (WT) plant 52 days after the in vitro plants were transplanted to soil according to an embodiment.

Figure 5C:
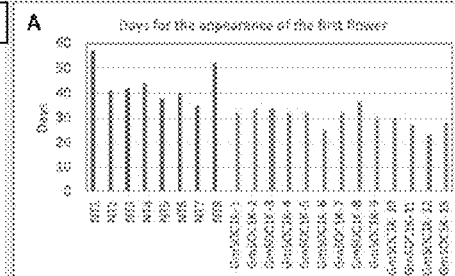
FIG. 5C is a graph showing days to produce first flower after $T_0$ plants were grown according to an embodiment.
Figure 5D:
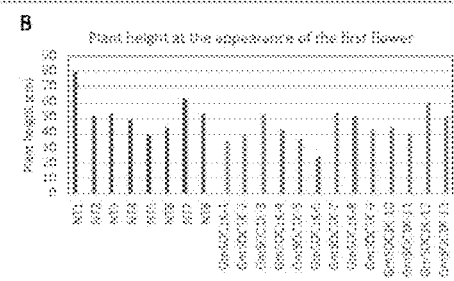
FIG. 5D is a graph showing plant height at the appearance of first flower after $T_0$ plants were grown according to an embodiment.
Figure 5E:
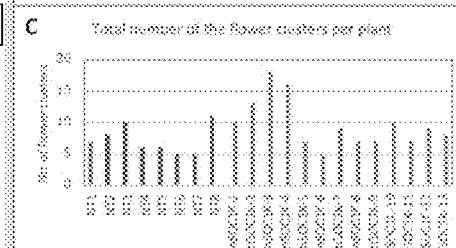
FIG. 5E is a graph showing total number of flower clusters per plant when $T_0$ plants were grown according to an embodiment.
Figure 5F:
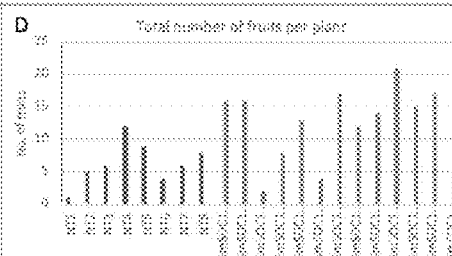
FIG. 5F is a graph showing total number of fruits per plant when $T_0$ plants were grown according to an embodiment.
Figure 5G:
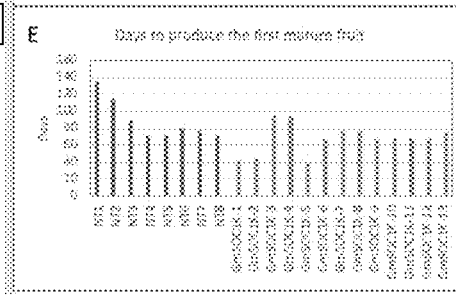
FIG. 5G is a graph showing the days to produce the first mature fruit when $T_0$ plants were grown according to an embodiment.
Figure 5H:
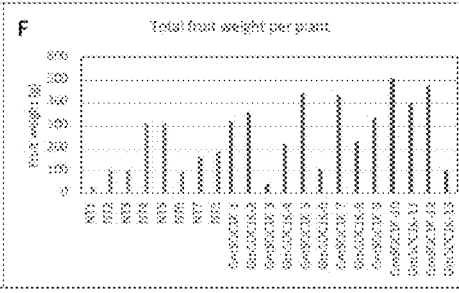
FIG. 5H is a graph showing total fruit weight (g) per plant when $T_0$ plants were grown according to an embodiment.

FIG. 5C is a graph showing the days elapsed to flower after $T_0$ plants were grown. FIG. 5D is a graph showing plant height at the appearance of first flower. FIG. 5E is a graph showing total number of flower clusters per plant. FIG. 5F is a graph showing total number of fruits per plant. FIG. 5G is a graph showing the days to produce the first mature fruit when $T_0$ plants were grown according to an embodiment. FIG. 5H is a graph showing total fruit weight (g) per plant when $T_0$ plants were grown according to an embodiment.

Constitutive expression of the GmSOC1K leads to high yields for tomato production.

The soybean SOC1-K domain construct was used to overexpress the soybean SOC1-K domain in soybean cultivars Jack and Williams 82. To this end, transformation of cotyledonary nodes was performed using *Agrobacterium tumefaciens* mediated transformation. Selection of the transformed $T_0$ plants were conducted using 10-20 mg/L hygromycin.

Plants were phenotyped and the $T_1$ transgenic plants and $T_1$ NT plants were compared. The results of overexpression of the rice SOC1-K domain lead to major phenotypic changes include flowering time, plant height, harvest time, etc Expression of soybean K-domain in soybean plants can result in major phenotypic changes such as, flowering time, plant height, branch number, harvest time, pod number, and/or pod weight per plant.

Example 8 (Prophetic)

The rice (*Oryza sativa*) SOC1-K domain can be constructed using procedures described in the Examples above. The DNA sequence of the rice K-domain is described in SEQUENCE ID NO: 31 and the amino acid sequence is described in SEQUENCE ID NO: 32. Briefly, the rice K-domain construct is driven by the CaMV 35S promoter (a strong constitutive promoter) and the OCS terminator. The Bar gene conferring herbicide resistance to bialophos or phosphinothricin can be selectable marker. Other selectable markers may be used. The rice SOC1-K domain construct can be used to ectopically overexpress the rice SOC1-K domain in rice plants or other plants. To this end, transformation of rice can be performed using *Agrobacterium tumefaciens* mediated transformation of mature seeds-derived embryogenic calluses of rice cultivar Nipponbare. Selection and regeneration of transgenic plants can be performed using 3-5 mg/L glufosinate ammonium.

Plants can be phenotyped and the $T_1$ transgenic plants and $T_1$ NT plants can be compared.

The results of overexpression of the rice SOC1-K domain lead to major phenotypic changes include flowering time, plant height, harvest time, etc.

In rice, the overexpression of rice SOC1-K-domain can result in fast-growing of the rice plants and an estimate of 10-25% increase of the yields.

Example 9 (Prophetic)

The canola (*Brassica napus*) SOC1-K domain can be constructed using procedures described in the Examples above. The DNA sequence of the canola K-domain is described in SEQUENCE ID NO: 31 and the amino acid sequence is described in SEQUENCE ID NO: 32. Briefly, the canola K-domain construct is driven by the CaMV 35S promoter (a strong constitutive promoter) and the OCS terminator. The Bar gene conferring herbicide resistance to bialophos or phosphinothricin can be selectable marker. Other selectable markers may be used. The canola SOC1-K domain construct can be used to ectopically overexpress the canola SOC1-K domain in canola plants or other plants. To this end, transformation of canola can be performed using *Agrobacterium tumefaciens* mediated transformation. Hypocotyledon segments of canola cultivar Westar can be inoculated with *Agrobacterium tumefaciens* containing the canola K-domain construct. Glufosinate ammonium can be used to select transgenic plants.

Plants can be phenotyped and the $T_1$ transgenic plants and $T_1$ NT plants can be compared.

The results of overexpression of the canola SOC1-K domain lead to major phenotypic changes include flowering time, plant height, harvest time, etc. In canola, the overexpression of rice SOC1-K-domain can result in fast-growing of the rice plants and an estimate of 10-25% increase of the yields.

Example 10 (Prophetic)

The cotton (*Gossypium hirsutum*) SOC1-K domain can be constructed using procedures described in the Examples above. The DNA sequence of the cotton K-domain is described in SEQUENCE ID NO: 31 and the amino acid sequence is described in SEQUENCE ID NO: 32. Briefly, the cotton K-domain construct is driven by the CaMV 35S promoter (a strong constitutive promoter) and the OCS terminator. The Bar gene conferring herbicide resistance to bialophos or phosphinothricin can be selectable marker. Other selectable markers may be used. The cotton SOC1-K domain construct can be used to ectopically overexpress the cotton SOC1-K domain in cotton plants or other plants. To this end, transformation of cotton can be performed using *Agrobacterium tumefaciens* mediated transformation. Hypocotyledon segments of regenerable cotton cultivar (e.g., Coker 312) can be inoculated with *Agrobacterium tumefaciens* containing the cotton SOC1-K domain.

Plants can be phenotyped and the $T_1$ transgenic plants and $T_1$ NT plants can be compared.

The results of overexpression of the cotton SOC1-K domain lead to major phenotypic changes include flowering time, plant height, harvest time, etc.

In cotton, the overexpression of cotton SOC1-K-domain can result in fast-growing of the cotton plants and an estimate of 10-25% increase of the yields.

In the various embodiments a method of producing a transgenic plant is provided comprising introducing a K-domain polypeptide encoded by a nucleotide sequence to produce a transformed cell.

In various embodiments, the polynucleotide is selected from a nucleotide sequence set forth in SEQ ID NO: 1; a nucleotide sequence encoding the polypeptide of SEQ ID NO: 2; a nucleotide sequence comprising at least 80% sequence identity to the sequence set forth in SEQ ID NO: 1; or a nucleotide sequence encoding an amino acid sequence having at least 90% sequence identity to the sequence set forth in SEQ ID NO: 2. In various embodiments the transformed cell is used to generate the transgenic plant, wherein the transgenic plant has increased expression of the K-domain polypeptide as compared to a control plant. In other embodiments, the sequences used in the method include introducing SEQ ID NO: 17, SEQ ID NO: 18 or SEQ ID NO: 19.

In various embodiments, a method of producing a transgenic plant is provided comprising introducing a SOC1K-domain polynucleotide. In various embodiments, the SOC1K-domain polynucleotide is from maize, rice, soybean, canola or cotton. In various embodiments, the polynucleotide is selected from a nucleotide sequence set forth in SEQ ID NO: 29, SEQ ID NO: 31, SEQ ID NO: 33, SEQ ID NO: 35 or SEQ ID NO: 37; or a nucleotide sequence comprising at least 90% sequence identity to the sequence set forth in SEQ ID NO: 29, SEQ ID NO: 31, SEQ ID NO: 33, SEQ ID NO: 35 or SEQ ID NO: 37; or a nucleotide sequence encoding an amino acid sequence of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 32, SEQ ID NO: 34, SEQ ID NO: 36 or SEQ ID NO: 38; or a nucleotide sequence encoding an amino acid sequence having at least 95% sequence identity to the sequence set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 32, SEQ ID NO: 34, SEQ ID NO: 36 or SEQ ID NO: 38. In various embodiments the transformed cell is used to generate the transgenic plant, wherein the transgenic plant has increased expression of the K-domain polypeptide as compared to a control plant.

In one embodiment, the K-domain sequence is a K-domain sequence of a MADS box gene.

In one embodiment, the plant used to produce the transgenic plant is a fruit-bearing plant.

In one embodiment, the method used to provide the transgenic plant is a blueberry plant. In other embodiments, the plant is selected from corn, rice, canola, sorghum, millet, soybean, tobacco, potato, wheat, cotton, peanut, rye, proso millet, foxtail millet, finger millet sunflower, safflower, wheat, sweet potato, cassava, pineapple, citrus trees, cocoa, tea, banana avocado, fig, sugarcane, oats, barley, vegetables, ornamentals, and conifers. In still other embodiments, the plant is selected from fruit-bearing plants such as grape, orange, lemon, grapefruit, avocado, date, peach, cherry, olive, plum, coconut, apple, pear blackberry, raspberry, strawberry, pineapple, tomato, cucumber and eggplant.

In various embodiments the method includes transgenic plants that comprise plant parts selected from an embryo, pollen, ovule, seed, leaf, flower, branch, fruit, kernel, ear, cob, husk stalk, root, root tips, anther, and combinations thereof.

In various embodiments, the method used to produce a transgenic plant is by stably transforming into a plant with a K-domain and variants of the K-domain. In various embodiments, the K-domain is maize K-domain, rice K-domain, soybean K-domain, cotton K-domain, canola K-domain and variants thereof are stably transformed into a plant to produce a transgenic plant.

In various embodiments, the transgenic plant has at least one characteristic selected from accelerated flowering time, reduced plant size, reduced leaf number, and combinations thereof.

In various embodiments, the method of producing transgenic plant with a K-domain polypeptide introduced into it exhibits increased yield compared to a control plant.

In various embodiments, the transgenic plant exhibits increased yield by at least 5%, 7%, 8% or 9%, compared to a control plant. In other embodiments, the transgenic plant exhibits increased yield by at least about 10 to 20% compared to a control plant. In still other embodiments, the transgenic plant exhibits increased yield by about 30% to about 50% compared to a control plant.

In various embodiments, an expression cassette useful for producing a transgenic plant comprising a polynucleotide encoding a K-domain polypeptide operably linked to a promoter that drives expression in a plant, wherein the polynucleotide is selected from:
  a nucleotide sequence set forth in SEQ ID NO: 1;
  a nucleotide sequence encoding the polypeptide of SEQ ID NO: 2;
  a nucleotide sequence comprising at least 80% sequence identity to the sequence set forth in SEQ ID NO: 1; and
  a nucleotide sequence encoding an amino acid sequence having at least 90% sequence identity to the sequence set forth in SEQ ID NO: 2.

In other embodiments, the sequences used in the expression cassette include SEQ ID NO: 3, SEQ ID NO: 17, SEQ ID NO: 18 or SEQ ID NO: 19. In one embodiment, the expression cassette comprises a constitutive promoter.

In various embodiments, an expression cassette producing a transgenic plant is provided comprising a polynucleotide encoding a K-domain polypeptide operably linked to a promoter that drives expression in a plant. In various embodiments, the K-domain polynucleotide is from maize, rice, soybean, canola or cotton. In various embodiments, the polynucleotide is selected from a nucleotide sequence set forth in SEQ ID NO: 29, SEQ ID NO: 31, SEQ ID NO: 33, SEQ ID NO: 35 or SEQ ID NO: 37; or a nucleotide sequence comprising at least 90% sequence identity to the sequence set forth in SEQ ID NO: 29, SEQ ID NO: 31, SEQ ID NO: 33, SEQ ID NO: 35 or SEQ ID NO: 37; or a nucleotide sequence encoding an amino acid sequence of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 32, SEQ ID NO: 34, SEQ ID NO: 36 or SEQ ID NO: 38; or a nucleotide sequence encoding an amino acid sequence having at least 95% sequence identity to the sequence set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 32, SEQ ID NO: 34, SEQ ID NO: 36 or SEQ ID NO: 38. In various embodiments the transformed cell is used to generate the transgenic plant, wherein the transgenic plant has increased expression of the K-domain polypeptide as compared to a control plant.

In one embodiment, an isolated host cell is transformed with the expression cassette in which a K-domain polypeptide operably linked to a promoter that drives expression in a plant, wherein the polynucleotide is selected from:
 a nucleotide sequence set forth in SEQ ID NO: 1;
 a nucleotide sequence encoding the polypeptide of SEQ ID NO: 2;
 a nucleotide sequence comprising at least 80% sequence identity to the sequence set forth in SEQ ID NO: 1; and
 a nucleotide sequence encoding an amino acid sequence having at least 90% sequence identity to the sequence set forth in SEQ ID NO: 2.

In various embodiments, an isolated host cell is transformed with the expression cassette in which a K-domain polypeptide operably linked to a promoter that drives expression in a plant. In various embodiments, the K-domain polynucleotide is from maize, rice, soybean, canola or cotton. In various embodiments, the polynucleotide is selected from a nucleotide sequence set forth in SEQ ID NO: 29, SEQ ID NO: 31, SEQ ID NO: 33, SEQ ID NO: 35 or SEQ ID NO: 37; or a nucleotide sequence comprising at least 90% sequence identity to the sequence set forth in SEQ ID NO: 29, SEQ ID NO: 31, SEQ ID NO: 33, SEQ ID NO: 35 or SEQ ID NO: 37; or a nucleotide sequence encoding an amino acid sequence of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 32, SEQ ID NO: 34, SEQ ID NO: 36 or SEQ ID NO: 38; or a nucleotide sequence encoding an amino acid sequence having at least 95% sequence identity to the sequence set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 32, SEQ ID NO: 34, SEQ ID NO: 36 or SEQ ID NO: 38.

In various embodiments, various plant parts may be transformed with the expression cassette. In still other embodiments, the various plant parts comprises plant parts selected from an embryo, pollen, ovule, seed, leaf, flower, branch, fruit, kernel, ear, cob, husk stalk, root, root tips, anther, and combinations thereof.

In various embodiments, the transgenic plant transformed with the expression cassette exhibits has at least one characteristic selected from accelerated flowering time, reduced plant size, reduced leaf number, and combinations thereof.

Various embodiments provide a transgenic plant comprising a plant transformed with a K-domain polypeptide encoded by a nucleotide sequence set forth in SEQ ID NO:1, wherein the transgenic plant has increased expression of the K-domain polypeptide compared to a control plant. In other embodiments, the plant may be transformed with SEQ ID NO:2, SEQ ID NO:3, SEQ ID NO:17, SEQ ID NO:18 or SEQ ID NO:19.

In one embodiment, the transgenic plant is a transgenic fruit-bearing plant. In other embodiments the transgenic plant is a blue berry plant. In other embodiments, the plants include grape, orange, lemon, grapefruit, avocado, date, peach, cherry, olive, plum, coconut, apple, pear blackberry, raspberry, strawberry, pineapple, tomato, cucumber and eggplant.

In still other embodiments, the transgenic plant is selected from corn, rice, sorghum, millet, soybean, tobacco, potato, wheat, cotton, peanut, rye, proso millet, foxtail millet, finger millet sunflower, safflower, wheat, sweet potato, cassava, pineapple, citrus trees, cocoa, tea, banana avocado, fig, sugarcane, oats, barley, vegetables, ornamentals, and conifers. In various embodiments, the transgenic plant has at least one altered characteristic selected from accelerated flowering time, reduced plant size, reduced leaf number, and combinations thereof.

In other embodiments, the transgenic plant exhibits increased yield compared to a control plant. In one embodiment, the transgenic plant exhibits increased yield compared to a plant not expressing the K-domain. In still other embodiments, the transgenic plant exhibits an increased yield by at least 5%, 7%, 8% or 9%, compared to a control plant. In other embodiments, the transgenic plant exhibits increased yield by at least about 10 to 20% compared to a control plant. In still other embodiments, the transgenic plant exhibits increased yield by about 30% to about 50% compared to a control plant.

In various embodiments, an expression cassette is provided comprising a polynucleotide. The polynucleotide comprises a nucleotide sequence encoding a K-domain polypeptide operably linked to a promoter that drives expression in a plant. The K-domain polypeptide is a K-domain of a MADS box polypeptide. The expression cassette further comprises a heterologous selectable marker wherein a transgenic plant expressing the nucleotide sequence has at least one characteristic selected from accelerated flowering time, reduced plant size, reduced leaf number, and combinations thereof compared to a control plant. In one embodiment, a transgenic plant comprises the expression cassette. In one embodiment, an isolated host cell is transformed with the expression cassette.

All patents, patent applications and literature cited in the specification are hereby incorporated by reference in their entirety. In the case of any inconsistencies, the present disclosure, including any definitions herein will prevail. Although specific embodiments have been illustrated and described herein, it will be appreciated by those of ordinary skill in the art that any procedure that is calculated to achieve the same purpose may be substituted for the specific embodiments shown. For example, although the process has been discussed using particular sequences, variations on the sequences and from different sources may be used. Additionally, although the process has been discussed using primarily tobacco, *petunia* and blueberry as the plant, other plants, such as soybean, corn, for example, may be used. This application is intended to cover any adaptations or variations of the present subject matter. Therefore, it is manifestly intended that embodiments of this invention be limited only by the claims and the equivalents thereof.

What is claimed is:

1. A method of producing a transgenic plant comprising: introducing a nucleotide sequence encoding a SOC1 or SOC1-like K-domain polypeptide into a plant cell to produce a transformed cell wherein the nucleotide sequence is selected from:
   a nucleotide sequence set forth in SEQ ID NO: 29, SEQ ID NO: 31, SEQ ID NO: 33, SEQ ID NO: 35;
   a nucleotide sequence encoding a polypeptide set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27 SEQ ID NO: 28, SEQ ID NO: 30, SEQ ID NO: 32, SEQ ID NO: 34 SEQ ID NO: 36, SEQ ID NO: 38;
   a nucleotide sequence encoding an amino acid sequence having at least 95% sequence identity to the sequences set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27 SEQ ID NO: 28, SEQ ID NO: 30, SEQ ID NO: 32, SEQ ID NO: 34 SEQ ID NO: 36, SEQ ID NO: 38; and
   regenerating the transgenic plant from the transformed cell, wherein the transgenic plant has increased expression of the K-domain polypeptide as compared to a control plant, wherein the polypeptide encoded by the polynucleotide sequence lacks the I-domain amino acid sequence and the C-domain amino acid sequence, wherein the transgenic plant has at least one characteristic selected from accelerated flowering time, reduced plant size, reduced leaf number, and combinations thereof compared to a control plant.

2. The method of claim 1 wherein the plant is a fruit-bearing plant.

3. The method of claim 2 wherein the fruit-bearing plant is selected from grape, orange, lemon, grapefruit, avocado, date, peach, cherry, olive, plum, coconut, apple, pear blackberry, blueberry, raspberry, strawberry, pineapple, tomato, cucumber and eggplant.

4. The method of claim 1 wherein the plant comprises plant parts selected from an embryo, pollen, ovule, seed, leaf, flower, branch, fruit, kernel, ear, cob, husk stalk, root, root tips, anther, and combinations thereof.

5. The method of claim 1 wherein the transgenic plant exhibits increased yield compared to a control plant.

6. The method of claim 1 wherein the plant is selected from corn, cotton, rice, soybean, canola, sugar beets, sunflower, potato, and safflower.

7. An expression cassette comprising:
   a polynucleotide comprising a nucleotide sequence encoding a SOC1 or SOC1-like K-domain polypeptide operably linked to a promoter that drives expression in a plant, wherein the nucleotide sequence is selected from:
   a nucleotide sequence set forth in SEQ ID NO: 29, SEQ ID NO: 31, SEQ ID NO: 33, SEQ ID NO: 35;
   a nucleotide sequence encoding a polypeptide set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27 SEQ ID NO: 28, SEQ ID NO: 30, SEQ ID NO: 32, SEQ ID NO: 34 SEQ ID NO: 36, SEQ ID NO: 38;
   a nucleotide sequence encoding an amino acid sequence having at least 95% sequence identity to the sequences set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27 SEQ ID NO: 28, SEQ ID NO: 30, SEQ ID NO: 32, SEQ ID NO: 34 SEQ ID NO: 36, SEQ ID NO: 38; and wherein the polypeptide encoded by the polynucleotide sequence lacks the I-domain amino acid sequence and the C-domain amino acid sequence, wherein the expression cassette further comprises a heterologous selectable marker and wherein a transgenic plant expressing said nucleotide sequence has at least one characteristic selected from accelerated flowering time, reduced plant size, reduced leaf number, and combinations thereof compared to a control plant.

8. The expression cassette of claim 7 wherein the promoter is a constitutive promoter.

9. An isolated host cell transformed with the expression cassette of claim 7.

10. A transgenic plant comprising a heterologous polynucleotide, wherein the heterologous polynucleotide comprises
a nucleotide sequence set forth in SEQ ID NO: 29, SEQ ID NO: 31, SEQ ID NO: 33, SEQ ID NO: 35;
a nucleotide sequence encoding a polypeptide set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27 SEQ ID NO: 28, SEQ ID NO: 30, SEQ ID NO: 32, SEQ ID NO: 34 SEQ ID NO: 36, SEQ ID NO: 38;
a nucleotide sequence encoding an amino acid sequence having at least 95% sequence identity to the sequences set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27 SEQ ID NO: 28, SEQ ID NO: 30, SEQ ID NO: 32, SEQ ID NO: 34 SEQ ID NO: 36, SEQ ID NO: 38, wherein the transgenic plant has increased expression of the K-domain polypeptide compared to a control plant, wherein the polypeptide encoded by the polynucleotide sequence lacks the I-domain amino acid sequence and the C-domain amino acid sequence, wherein the transgenic plant has at least one characteristic selected from accelerated flowering time, reduced plant size, reduced leaf number, and combinations thereof compared to a control plant.

11. The transgenic plant of claim 10 wherein the transgenic plant is a transgenic fruit-bearing plant.

12. The transgenic plant of claim 10 wherein the plant is selected from grape, orange, lemon, grapefruit, avocado, date, peach, cherry, olive, plum, coconut, apple, pear blackberry, blueberry, raspberry, strawberry, pineapple, tomato, cucumber and eggplant.

13. The transgenic plant of claim 10 wherein the transgenic plant exhibits increased yield compared to a control plant.

14. The transgenic plant of claim 10 wherein the plant is selected from corn, cotton, rice, soybean, canola, sugar beets, sunflower, potato, and safflower.

15. A transgenic plant comprising the expression cassette of claim 7.

16. The transgenic plant of claim 15 wherein the plant is selected from corn, cotton, rice, soybean, canola, sugar beets, sunflower, potato, safflower, grape, orange, lemon, grapefruit, avocado, date, peach, cherry, olive, plum, coconut, apple, pear blackberry, blueberry, raspberry, strawberry, pineapple, tomato, cucumber and eggplant.

17. An expression cassette comprising:
a polynucleotide comprising a nucleotide sequence encoding a K-domain polypeptide operably linked to a promoter that drives expression in a plant, wherein the K-domain polypeptide is a SOC1 or SOC1-like K-domain of a MADS box polypeptide, wherein the polypeptide encoded by the polynucleotide sequence lacks the I-domain amino acid sequence and the C-domain amino acid sequence, and wherein the expression cassette further comprises a heterologous selectable marker and wherein a transgenic plant expressing said nucleotide sequence has at least one characteristic selected from accelerated flowering time, reduced plant size, reduced leaf number, and combinations thereof compared to a control plant.

18. A transgenic plant comprising the expression cassette of claim 17.

19. An isolated host cell transformed with the expression cassette of claim 17.

20. An expression cassette comprising:
a polynucleotide comprising a nucleotide sequence encoding a K-domain polypeptide operably linked to a promoter that drives expression in a plant, wherein the nucleotide sequence is selected from:
a nucleotide sequence set forth in SEQ ID NO: 29, SEQ ID NO: 31, SEQ ID NO: 33, SEQ ID NO: 35;
a nucleotide sequence encoding a polypeptide set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27 SEQ ID NO: 28, SEQ ID NO: 30, SEQ ID NO: 32, SEQ ID NO: 34 SEQ ID NO: 36, SEQ ID NO: 38;
a nucleotide sequence encoding an amino acid sequence having at least 95% sequence identity to the sequences set forth in SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27 SEQ ID NO: 28, SEQ ID NO: 32, SEQ ID NO: 34 SEQ ID NO: 36, SEQ ID NO: 38; and wherein the polypeptide encoded by the polynucleotide sequence lacks the I-domain amino acid sequence and the C-domain amino acid sequence, wherein the expression cassette further comprises a heterologous selectable marker and wherein a transgenic plant expressing said nucleotide sequence has at least one characteristic selected from accelerated flowering time, reduced plant size, reduced leaf number, and combinations thereof compared to a control plant.

* * * * *

SEQUENCE LISTING

<160> NUMBER OF SEQ ID NOS: 38

<210> SEQ ID NO 1
<211> LENGTH: 474
<212> TYPE: DNA
<213> ORGANISM: Vaccinium corymbosum

<400> SEQUENCE: 1

```
atgcaggaga ctatacagcg ataccagagg cgaataaaag aagttcaaat cgacaaatca      60
ttagtcgaac aaaacatgca gcacttgaag catgaagcag cagacatgtc aaagaagata     120
gagcatcttg aagttgcaaa gcgcaaactc ttgggggaag gtctggggtc atgcaccttt     180
gaagaactta tacaaattga caacagttga gagcagagcg caagcacaat ccgggcaaga     240
aagatgcaag ttttcaggga acagattgag aaacttaaag agaaggagaa agccctagaa     300
gccgaaaatg caatgctatg tgtgaagcat ggcctacaac cacggaaaga atcaaatgaa     360
gatcagggag agaatgagca atccacagaa actaatgaga actcagatgt ggaaactgaa     420
ttattcatcg gaccgcctga ggggagaatt aagcgagttt cgccacccaa gtga          474
```

<210> SEQ ID NO 2
<211> LENGTH: 218
<212> TYPE: PRT
<213> ORGANISM: Vaccinium corymbosum

<400> SEQUENCE: 2

```
Met Val Arg Gly Lys Thr Gln Met Arg Arg Ile Glu Asn Ala Thr Ser
1               5                  10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ala Leu Ile Val Phe
        35                  40                  45

Ser Pro Arg Gly Lys Leu Tyr Glu Phe Ala Ser Ser Met Gln Glu
    50                  55                  60

Thr Ile Gln Arg Tyr Gln Arg Arg Ile Lys Glu Val Gln Ile Asp Lys
65                  70                  75                  80

Ser Leu Val Glu Gln Asn Met Gln His Leu Lys His Glu Ala Ala Asp
                85                  90                  95

Met Ser Lys Lys Ile Glu His Leu Glu Val Ala Lys Arg Lys Leu Leu
            100                 105                 110

Gly Glu Gly Leu Gly Ser Cys Thr Leu Glu Glu Leu Ile Gln Ile Glu
        115                 120                 125

Gln Gln Leu Glu Gln Ser Ala Ser Thr Ile Arg Ala Arg Lys Met Gln
    130                 135                 140

Val Phe Arg Glu Gln Ile Glu Lys Leu Lys Glu Lys Glu Lys Ala Leu
145                 150                 155                 160

Glu Ala Glu Asn Ala Met Leu Cys Val Lys His Gly Leu Gln Pro Arg
                165                 170                 175

Lys Glu Ser Asn Glu Asp Gln Gly Glu Asn Glu Gln Ser Thr Glu Thr
            180                 185                 190

Asn Glu Asn Ser Asp Val Glu Thr Glu Leu Phe Ile Gly Pro Pro Glu
        195                 200                 205

Gly Arg Thr Lys Arg Val Ser Pro Pro Lys
    210                 215
```

<210> SEQ ID NO 3
<211> LENGTH: 656

<212> TYPE: DNA
<213> ORGANISM: Vaccinium corymbosum

<400> SEQUENCE: 3

```
atggtgagag ggaaaaccca gatgaggcgt atagaaaacg ccacaagcag gcaagtcacc      60
ttctccaaga ggaggaacgg gctcctcaaa aggccttcga gctttcggtc ctttgcgatg     120
ccgaggttgc cctcatcgtc ttctctccaa gaggaaagct ctacgaattc gctagctcca     180
gcatgcagga gactatacag cgataccaga ggcgaataaa agaagttcaa attgacaaat     240
cattagtcga acaaaacatg cagcacttga agcatgaagc agcagacatg tcaaagaaga     300
tagagcatct tgaagttgca aagcgcaaac tcttggggga aggtctgggg tcttgcaccc     360
ttgaagaact tatacaaatt gaacaacagt tggagcagag cgcaagcaca atccgggcaa     420
gaaagatgca gttttcagg gaacagattg agaaacttaa agagaaggag aaagccctag      480
aagccgaaaa tgcaatgcta tgtgtgaagc atggcctaca accacggaaa gaatcaaatg     540
aagatcaggg agagaatgag caatccacag aaactaatga gaactcagat gtggaaactg     600
aattattcat cggaccgcct gaggggagaa ctaagcgagt ttcgccaccc aagtga        656
```

<210> SEQ ID NO 4
<211> LENGTH: 20
<212> TYPE: DNA
<213> ORGANISM: Artificial Sequence
<220> FEATURE:
<223> OTHER INFORMATION: SOCF1

<400> SEQUENCE: 4

```
attgcacgta tccaatgctt                                                  20
```

<210> SEQ ID NO 5
<211> LENGTH: 20
<212> TYPE: DNA
<213> ORGANISM: Artificial Sequence
<220> FEATURE:
<223> OTHER INFORMATION: SOCR1

<400> SEQUENCE: 5

```
ccaagaggaa agctctacga                                                  20
```

<210> SEQ ID NO 6
<211> LENGTH: 25
<212> TYPE: DNA
<213> ORGANISM: Artificial Sequence
<220> FEATURE:
<223> OTHER INFORMATION: SOF1

<400> SEQUENCE: 6

```
tctagaatgc aggagactat acagc                                            25
```

<210> SEQ ID NO 7
<211> LENGTH: 25
<212> TYPE: DNA
<213> ORGANISM: Artificial Sequence
<220> FEATURE:
<223> OTHER INFORMATION: SOK

<400> SEQUENCE: 7

```
ggtacctcac ttgggtggcg aaact                                            25
```

<210> SEQ ID NO 8
<211> LENGTH: 20
<212> TYPE: DNA

```
<213> ORGANISM: Artificial Sequence
<220> FEATURE:
<223> OTHER INFORMATION: 35S-F

<400> SEQUENCE: 8
tgacgcacaa tcccactatc                                                20

<210> SEQ ID NO 9
<211> LENGTH: 21
<212> TYPE: DNA
<213> ORGANISM: Artificial Sequence
<220> FEATURE:
<223> OTHER INFORMATION: NPTII-F

<400> SEQUENCE: 9
gaggctattc ggctatgact g                                              21

<210> SEQ ID NO 10
<211> LENGTH: 21
<212> TYPE: DNA
<213> ORGANISM: Artificial Sequence
<220> FEATURE:
<223> OTHER INFORMATION: NPTII-R

<400> SEQUENCE: 10
atcgggagcg gcgataccgt a                                              21

<210> SEQ ID NO 11
<211> LENGTH: 20
<212> TYPE: DNA
<213> ORGANISM: Artificial Sequence
<220> FEATURE:
<223> OTHER INFORMATION: Actin-F

<400> SEQUENCE: 11
gtgttggact ctggtgatgg                                                20

<210> SEQ ID NO 12
<211> LENGTH: 20
<212> TYPE: DNA
<213> ORGANISM: Artificial Sequence
<220> FEATURE:
<223> OTHER INFORMATION: Actin-R

<400> SEQUENCE: 12
tcagcagtgg tggtgaacat                                                20

<210> SEQ ID NO 13
<211> LENGTH: 17
<212> TYPE: DNA
<213> ORGANISM: Artificial Sequence
<220> FEATURE:
<223> OTHER INFORMATION: BBK-domain - F

<400> SEQUENCE: 13
ggagcagagc gcaagca                                                   17

<210> SEQ ID NO 14
<211> LENGTH: 23
<212> TYPE: DNA
<213> ORGANISM: Artificial Sequence
<220> FEATURE:
<223> OTHER INFORMATION: BBK-domain - R

<400> SEQUENCE: 14
aatctgttcc ctgaaaactt gca                                            23
```

<210> SEQ ID NO 15
<211> LENGTH: 28
<212> TYPE: DNA
<213> ORGANISM: Artificial Sequence
<220> FEATURE:
<223> OTHER INFORMATION: BOC-FX

<400> SEQUENCE: 15
tctagaatgg tgagagggaa aacccaga                                28

<210> SEQ ID NO 16
<211> LENGTH: 23
<212> TYPE: DNA
<213> ORGANISM: Artificial Sequence
<220> FEATURE:
<223> OTHER INFORMATION: BOC-RS

<400> SEQUENCE: 16
gagctcactt gggtggcgaa act                                     23

<210> SEQ ID NO 17
<211> LENGTH: 657
<212> TYPE: DNA
<213> ORGANISM: Vaccinium corymbosum

<400> SEQUENCE: 17
atggtgagag ggaaaaccca gatgaggcgt atagaaaacg ccacaagcag gcaagtcacc    60
ttttccaaga ggagggacgg gctcctcaaa aaggccttcg agctttcggt tctttgcgat   120
gccgaggttg ccctcatcgt cttctctcca agaggaaagc tctacgaatt cgctagctcc   180
agcatgcagg agactataca gcgataccag aggcgaataa agaagttca aatcgacaaa    240 tcattagtcg aacaaaacat gcagcacttg aagcatgaag cagcagacat gtcaaagaag   300
atagagcatc ttgaagttgc aaagcgcaaa ctcttggggg aaggtctggg gtcgtgcacc   360
tttgaagaac ttatacaaat tgaacaacag ttggagcaga gcgcaagcac aatccgggca   420
agaaagatgc aagttttcag ggaacagatt gagaaactta agagaagga gaaagcccta    480 gaagccgaaa atgcaatgct atgcgtgaag catggcctac aaccacggaa agaatcaaat   540
gaagatcagg gagagaatga gcaatccaca gaaactaatg agaactcaga tgtggaaact   600
gaattattca tcggaccgcc tgaggggaga actaagcgag tttcgccacc caagtga      657

<210> SEQ ID NO 18
<211> LENGTH: 576
<212> TYPE: DNA
<213> ORGANISM: Vaccinium corymbosum

<400> SEQUENCE: 18
atggtgagag ggaaaaccca gatgaggcgt atagaaaacg ccacaagcag gcaagtcgtc    60
ttctctccaa gaggaaagct ctacgaattc gctagctcca gcatgcagga gactatacag   120
cgataccaga ggcgaataaa agaagttcaa attgacaaat cattagtcga acaaaacatg   180
cagcacttga agcatgaagc agcagacatg tcaaagaaga tagagcatct tgaagttgca   240
aagcgcaaac tcttgggggga aggtctgggg tcatgcacct ttgaagaact tatacaaatt   300
gaacaacagt tggagcagag cgcaagcaca atccgggcaa gaaagatgca agttttcagg   360
gaacagattg agaaacttaa agagaaggag aaagccctag aagccgaaaa tgcaatgcta   420
tgtgtgaagc atggcctaca accacggaaa gaatcaaatg aagatcaggg agagaatgag   480

```
caatccacag aaactaatga gaactcagat gtggaaactg aattattcat cggaccgcct    540
gaggggagaa ttaagcgagt tcgccacccc aagtga                              576
```

<210> SEQ ID NO 19
<211> LENGTH: 654
<212> TYPE: DNA
<213> ORGANISM: Vaccinium corymbosum

<400> SEQUENCE: 19

```
atggtgagag ggaaaaccca gatgaggcgt atagaaaacg ccacaagcag gcaagtcacc     60
ttctccaaga ggaggaacgg gctcctcaag aaggccttcg agctttcggt cctttgcgat    120
gccgaggttg ccctcatcgt cttctctcca agaggaaagc tctacgaatt cgctagctcc    180
agcatgcagg agactataca gcgataccag aggcgaataa agaagttca aatcgacaaa     240 tcattagtcg aacaaaacat gcagcacttg aagcatgaag cagcagacat gtcaaagaag    300
atagagcatc ttgaagttgc aaagcgcaaa ctcttggggg aaggtctggg gtcgtgcacc    360
tttgaagaac ttatacaaat tgaacaacag ttggagcaga gcgcaagcac aatccgggca    420
agaaagatgc aagttttcag ggaacagatt gagaaactta agagaagaa agccctagaa     480 gccgaaaatg caatgctatg tgtgaagcat ggcctacaac cacggaaaga atcaaatgaa    540
gatcagggag agaatgagca atccacagaa actaatgaga actcagatgt ggaaactgaa    600
ttattcatcg accgcctga ggggagaact aagcgagttt cgccaccca gtga             654
```

<210> SEQ ID NO 20
<211> LENGTH: 84
<212> TYPE: PRT
<213> ORGANISM: Vaccinium corymbosum

<400> SEQUENCE: 20

```
Glu Gln Asn Met Gln His Leu Lys His Glu Ala Ala Asp Met Ser Lys
1               5                   10                  15

Lys Ile Glu His Leu Glu Val Ala Lys Arg Lys Leu Leu Gly Glu Gly
            20                  25                  30

Leu Gly Ser Cys Thr Phe Glu Glu Leu Ile Gln Ile Glu Gln Gln Leu
        35                  40                  45

Glu Gln Ser Ala Ser Thr Ile Arg Ala Arg Lys Met Gln Val Phe Arg
    50                  55                  60

Glu Gln Ile Glu Lys Leu Lys Glu Lys Glu Lys Ala Leu Glu Ala Glu
65                  70                  75                  80

Asn Ala Met Leu
```

<210> SEQ ID NO 21
<211> LENGTH: 84
<212> TYPE: PRT
<213> ORGANISM: Nicotiana tabacum

<400> SEQUENCE: 21

```
Glu Gln Asn Leu Gln His Met Gln His Ala Ala Ala Ser Leu Met Lys
1               5                   10                  15

Lys Ile Glu Leu Leu Glu Glu Ser Lys Arg Lys Leu Leu Gly Glu Gly
            20                  25                  30

Leu Gln Ser Cys Ser Leu Val Glu Leu Gln Gln Ile Glu Lys Gln Leu
        35                  40                  45

Glu Arg Ser Val Ser Thr Ile Arg Ala Arg Lys Ile Gln Val Phe Lys
    50                  55                  60
```

Glu Gln Ile Glu Arg Leu Lys Glu Lys Glu Ile Leu Ala Ser Glu
65                  70                  75                  80

Asn Ala Ile Leu

<210> SEQ ID NO 22
<211> LENGTH: 84
<212> TYPE: PRT
<213> ORGANISM: Populus trichocarpa

<400> SEQUENCE: 22

Glu Gln Asn Met Leu Gln Leu Lys Glu Ala Ala Ser Met Ile Lys
1               5                   10                  15

Lys Ile Glu His Leu Glu Val Ser Lys Arg Lys Leu Leu Gly Glu Cys
                20                  25                  30

Leu Gly Ser Cys Thr Val Glu Glu Leu Gln Gln Ile Glu Gln Gln Leu
            35                  40                  45

Glu Arg Ser Val Ser Thr Ile Arg Ala Arg Lys Asn Gln Val Phe Lys
        50                  55                  60

Glu Gln Ile Glu Leu Leu Arg Gln Lys Glu Lys Leu Leu Ala Ala Glu
65                  70                  75                  80

Asn Ala Arg Leu

<210> SEQ ID NO 23
<211> LENGTH: 84
<212> TYPE: PRT
<213> ORGANISM: Populus tremuloides

<400> SEQUENCE: 23

Glu Gln Asn Met Leu Gln Leu Lys Glu Ala Ala Ser Met Ile Lys
1               5                   10                  15

Lys Ile Glu His Leu Glu Val Ser Lys Arg Lys Leu Leu Gly Glu Cys
                20                  25                  30

Leu Gly Ser Cys Thr Ile Glu Glu Leu Gln Gln Ile Glu Gln Gln Leu
            35                  40                  45

Glu Arg Ser Val Ser Thr Ile Arg Ala Arg Lys Asn Gln Val Phe Lys
        50                  55                  60

Glu Gln Ile Glu Leu Leu Lys Gln Lys Glu Lys Leu Leu Ala Ala Glu
65                  70                  75                  80

Asn Ala Arg Leu

<210> SEQ ID NO 24
<211> LENGTH: 84
<212> TYPE: PRT
<213> ORGANISM: Prunus mume

<400> SEQUENCE: 24

Asp Gln Asn Met Gln His Leu Lys Gln Glu Ser Ser Met Met Lys
1               5                   10                  15

Gln Ile Glu Leu Leu Glu Val Ser Lys Arg Lys Leu Leu Gly Glu Gly
                20                  25                  30

Leu Gly Ser Cys Ser Ile Glu Glu Leu Gln Glu Ile Glu Gln Gln Leu
            35                  40                  45

Glu Arg Ser Val Ser Asn Val Arg Ala Arg Lys Thr Gln Val Phe Lys
        50                  55                  60

Glu Gln Ile Glu Gln Leu Arg Glu Lys Gly Lys Ala Leu Ala Ala Glu
65                  70                  75                  80

Asn Glu Lys Leu

<210> SEQ ID NO 25
<211> LENGTH: 84
<212> TYPE: PRT
<213> ORGANISM: Malus domestica

<400> SEQUENCE: 25

Glu Gln Asn Met Gln His Leu Lys Gln Glu Ala Thr Ser Met Met Lys
1               5                   10                  15

Gln Ile Glu Leu Leu Glu Val Ser Lys Arg Lys Leu Leu Gly Glu Gly
            20                  25                  30

Leu Gly Ser Cys Thr Leu Ala Glu Leu Gln Glu Ile Glu Asp Gln Leu
        35                  40                  45

Glu Lys Ser Val Tyr Asn Val Arg Ala Arg Lys Ser Gln Val Phe Lys
50                  55                  60

Glu Gln Ile Glu Gln Leu Arg Glu Lys Glu Lys Leu Leu Thr Ala Glu
65                  70                  75                  80

Asn Thr Arg Leu

<210> SEQ ID NO 26
<211> LENGTH: 84
<212> TYPE: PRT
<213> ORGANISM: Arabidopsis thaliana

<400> SEQUENCE: 26

Glu Glu Asn Met Gln His Leu Lys Tyr Glu Ala Ala Asn Met Met Lys
1               5                   10                  15

Lys Ile Glu Gln Leu Glu Ala Ser Lys Arg Lys Leu Leu Gly Glu Gly
            20                  25                  30

Ile Gly Thr Cys Ser Ile Glu Glu Leu Gln Gln Ile Glu Gln Gln Leu
        35                  40                  45

Glu Lys Ser Val Lys Cys Ile Arg Ala Arg Lys Thr Gln Val Phe Lys
50                  55                  60

Glu Gln Ile Glu Gln Leu Lys Gln Lys Glu Lys Ala Leu Ala Ala Glu
65                  70                  75                  80

Asn Glu Lys Leu

<210> SEQ ID NO 27
<211> LENGTH: 84
<212> TYPE: PRT
<213> ORGANISM: Vitis vinifera

<400> SEQUENCE: 27

Glu His Asn Met Gln His Leu Lys His Glu Ala Ala Asn Met Ala Lys
1               5                   10                  15

Lys Ile Glu Leu Leu Glu Ile Ser Lys Arg Lys Leu Leu Gly Glu Gly
            20                  25                  30

Leu Gly Ser Cys Ser Ile Glu Glu Leu Gln Gln Ile Glu Gln Gln Leu
        35                  40                  45

Glu Arg Ser Val Ser Ser Ile Arg Ala Arg Lys Asn Gln Val Phe Lys
50                  55                  60

Glu Gln Ile Glu Gln Leu Lys Glu Lys Glu Lys Ala Leu Ala Ala Glu
65                  70                  75                  80

Asn Ala Met Leu

<210> SEQ ID NO 28
<211> LENGTH: 84

<212> TYPE: PRT
<213> ORGANISM: Citrus sinensis

<400> SEQUENCE: 28

```
Glu Arg Tyr Met Gln Gln Leu Lys His Glu Ile Ala Asn Met Ile Glu
1               5                   10                  15

Lys Ile Glu His Ile Glu Val Ser Gln Arg Lys Leu Leu Gly Gln Asp
            20                  25                  30

Leu Gly Ser Arg Thr Asn Glu Glu Leu Gln Glu Leu Asp Asp Gln Leu
        35                  40                  45

Glu Arg Ser Leu Arg Ser Ile Arg Ala Arg Lys Ala Gln Leu Phe Asn
50                  55                  60

Glu Gln Met Gly Gln Leu Lys Glu Lys Glu Arg Leu Leu Leu Glu Asp
65                  70                  75                  80

Asn Ala Arg Leu
```

<210> SEQ ID NO 29
<211> LENGTH: 696
<212> TYPE: DNA
<213> ORGANISM: Zea mays

<400> SEQUENCE: 29

```
atggtgcggg gcaagacgca gatgaagcgg atagagaacc cgaccagccg ccaggtcacc    60
ttctccaagc gccgcaacgg cctgctcaag aaggcgttcg agctctccgt cctctgcgac   120
gccgaggtcg ccctcgtcgt cttctccccg cgcggcaagc tctacgaatt cgccagcgga   180
agtgcgcaga aaacgattga acgttataga acatacacaa aggataatgt cagcaacaag   240
acagtgcagc aggatattga gcgagtaaaa gctgatgcgg atggcctgtc aaagagactc   300
gaagcacttg aagcttacaa aaggaaactt ttgggtgaga ggttggaaga ctgctccatt   360
gaagagctgc acagtttgga agtcaagctt gagaagagcc tgcattgcat caggggaaga   420
aagactgagc tgctggagga gcaagtccgt aagctgaagc agaaggagat gagtctgcgc   480
aagagcaacg aagatttgcg tgaaaagtgc aagaagcagc cgcctgtgcc gatggcttcg   540
gcgccgcctc gtcgccggc agtcgacaac gtggaggacg tcaccggga gccgaaggac   600
gacgggatgg acgtggagac ggagctgtac ataggattgc ccggcagaga ctaccgctca   660
agcaaagaca aggctgcagt ggcggtcagg tcaggc                             696
```

<210> SEQ ID NO 30
<211> LENGTH: 232
<212> TYPE: PRT
<213> ORGANISM: Zea mays

<400> SEQUENCE: 30

```
Met Val Arg Gly Lys Thr Gln Met Lys Arg Ile Glu Asn Pro Thr Ser
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ala Leu Val Val Phe
        35                  40                  45

Ser Pro Arg Gly Lys Leu Tyr Glu Phe Ala Ser Gly Ser Ala Gln Lys
    50                  55                  60

Thr Ile Glu Arg Tyr Arg Thr Tyr Thr Lys Asp Asn Val Ser Asn Lys
65                  70                  75                  80

Thr Val Gln Gln Asp Ile Glu Arg Val Lys Ala Asp Ala Asp Gly Leu
                85                  90                  95
```

```
Ser Lys Arg Leu Glu Ala Leu Glu Ala Tyr Lys Arg Lys Leu Leu Gly
            100                 105                 110

Glu Arg Leu Glu Asp Cys Ser Ile Glu Leu His Ser Leu Glu Val
        115                 120                 125

Lys Leu Glu Lys Ser Leu His Cys Ile Arg Gly Arg Lys Thr Glu Leu
    130                 135                 140

Leu Glu Glu Gln Val Arg Lys Leu Lys Gln Lys Glu Met Ser Leu Arg
145                 150                 155                 160

Lys Ser Asn Glu Asp Leu Arg Glu Lys Cys Lys Lys Gln Pro Pro Val
                165                 170                 175

Pro Met Ala Ser Ala Pro Pro Arg Ala Pro Ala Val Asp Asn Val Glu
            180                 185                 190

Asp Gly His Arg Glu Pro Lys Asp Asp Gly Met Asp Val Glu Thr Glu
        195                 200                 205

Leu Tyr Ile Gly Leu Pro Gly Arg Asp Tyr Arg Ser Ser Lys Asp Lys
    210                 215                 220

Ala Ala Val Ala Val Arg Ser Gly
225                 230

<210> SEQ ID NO 31
<211> LENGTH: 702
<212> TYPE: DNA
<213> ORGANISM: Oryza sativa

<400> SEQUENCE: 31
atggtgcggg ggaggacgga gctgaagcgg attgagaacc cgacgagccg gcaggtgacc        60
ttctccaagc gccggaatgg cctcctcaag aaggcgttcg agctctccgt cctctgcgac       120
gccgaggtcg ccctcatcgt cttctccccc gcggccgcc tctacgagtt cgccagcgcc        180
cccagcctac agaaaaccat cgaccgctat aaagcataca caaggatca tgtcaacaat        240 aagacaattc aacaagatat ccagcaagtc aaagatgata ctttaggctt ggccaagaaa       300
cttgaagctc ttgatgagtc cagacggaaa atattgggag aaaatttaga aggattctct       360
attgaagaac tgcgtggtct agaaatgaaa cttgagaaga gcctccacaa gataagacta       420
aagaagaccg agcttctgga gcagcagata gccaagctga agagaagga gcggactttg         480 cttaaagaca acgaaaattt acgcggaaag catcgcaacc ttgaggctgc ggcgctggtg       540
gctaaccaca tgacgacgac gacggcgccg gcggcgtggc cgcgggacgt gcctatgacg       600
agcagcacag ccggcgccgc cgacgccatg gacgtggaga ctgatctgta cattggattg       660
cccggcactg agcgctcctc caaccggtcg gagacaggtt ga                         702

<210> SEQ ID NO 32
<211> LENGTH: 233
<212> TYPE: PRT
<213> ORGANISM: Oryza sativa

<400> SEQUENCE: 32

Met Val Arg Gly Arg Thr Glu Leu Lys Arg Ile Glu Asn Pro Thr Ser
1               5                   10                  15

Arg Gln Val Thr Phe Ser Lys Arg Asn Gly Leu Leu Lys Lys Ala
            20                  25                  30

Phe Glu Leu Ser Val Leu Cys Asp Ala Glu Val Ala Leu Ile Val Phe
        35                  40                  45

Ser Pro Arg Gly Arg Leu Tyr Glu Phe Ala Ser Ala Pro Ser Leu Gln
    50                  55                  60
```

```
Lys Thr Ile Asp Arg Tyr Lys Ala Tyr Thr Lys Asp His Val Asn Asn
 65                  70                  75                  80

Lys Thr Ile Gln Gln Asp Ile Gln Gln Val Lys Asp Asp Thr Leu Gly
                 85                  90                  95

Leu Ala Lys Lys Leu Glu Ala Leu Asp Glu Ser Arg Arg Lys Ile Leu
            100                 105                 110

Gly Glu Asn Leu Glu Gly Phe Ser Ile Glu Glu Leu Arg Gly Leu Glu
        115                 120                 125

Met Lys Leu Glu Lys Ser Leu His Lys Ile Arg Leu Lys Lys Thr Glu
    130                 135                 140

Leu Leu Glu Gln Gln Ile Ala Lys Leu Lys Glu Lys Glu Arg Thr Leu
145                 150                 155                 160

Leu Lys Asp Asn Glu Asn Leu Arg Gly Lys His Arg Asn Leu Glu Ala
                165                 170                 175

Ala Ala Leu Val Ala Asn His Met Thr Thr Thr Ala Pro Ala Ala
            180                 185                 190

Trp Pro Arg Asp Val Pro Met Thr Ser Thr Ala Gly Ala Ala Asp
        195                 200                 205

Ala Met Asp Val Glu Thr Asp Leu Tyr Ile Gly Leu Pro Gly Thr Glu
    210                 215                 220

Arg Ser Ser Asn Arg Ser Glu Thr Gly
225                 230

<210> SEQ ID NO 33
<211> LENGTH: 630
<212> TYPE: DNA
<213> ORGANISM: Glycine max

<400> SEQUENCE: 33
atggtgagag gaaagactca gatgaggcgc atagagaacg ccacaagcag gcaagtcacc      60
ttctcaaagc ggcgtaatgg gttgctgaag aaggcctttg aactttctgt tctttgtgat     120
gctgaggttg ctctcatcat tttctctcca agaggaaagc tttatgaatt tgcaagctcc     180
agcatgcagg acacaattga acgctaccgc aggcataaca ggagtgctca acagtgaac     240 agatctgatg aacaaaatat gcagcatttg aagcaagaaa cagcaaactt gatgaagaag     300
attgagcttc ttgaggcttc aaaacggaag ctcttgggag aaggtttggg gtcatgctcc     360
ttagaagaac tgcaacagat agaacaacaa ttggaaagga gtgtaagcaa tgttcgtgca     420
agaaagaatc aagtttacaa ggaacaaatt gatcaactaa agagaagga aagagctcta      480 tatgctgaaa atgctaggct gtgtgagcag tatggtatcc agccacagcc agcaacaaag     540
gatccgaaag aaattcaacc ctatgcagaa agcagtccaa gttcagaagt ggagactgaa     600
ttgttcattg gactacccag gtctatctag                                       630

<210> SEQ ID NO 34
<211> LENGTH: 209
<212> TYPE: PRT
<213> ORGANISM: Glycine max

<400> SEQUENCE: 34

Met Val Arg Gly Lys Thr Gln Met Arg Arg Ile Glu Asn Ala Thr Ser
 1               5                  10                  15

Arg Gln Val Thr Pro Ser Lys Arg Arg Asn Gly Leu Leu Lys Lys Ala
             20                  25                  30

Phe Glu Leu Ser Val Leu Cys Asp Ala Glu Val Ala Leu Ile Ile Phe
```

```
            35                  40                  45
Ser Pro Arg Gly Lys Leu Tyr Glu Phe Ala Ser Ser Met Gln Asp
    50                  55                  60

Thr Ile Glu Arg Tyr Arg Arg His Asn Arg Ser Ala Gln Thr Val Asn
65                  70                  75                  80

Asp Ser Asp Glu Gln Asn Met Gln His Leu Lys Gln Glu Thr Ala Asn
                85                  90                  95

Leu Met Lys Lys Ile Glu Leu Leu Glu Ala Ser Lys Arg Lys Leu Leu
            100                 105                 110

Gly Glu Gly Leu Gly Ser Cys Ser Leu Glu Glu Leu Gln Gln Ile Glu
        115                 120                 125

Gln Gln Leu Glu Arg Ser Val Ser Asn Val Arg Ala Arg Lys Asn Gln
    130                 135                 140

Val Tyr Lys Glu Gln Ile Asp Gln Leu Lys Glu Lys Glu Arg Ala Leu
145                 150                 155                 160

Tyr Ala Glu Asn Ala Arg Leu Cys Glu Gln Tyr Gly Ile Gln Pro Gln
                165                 170                 175

Pro Ala Thr Lys Asp Pro Lys Glu Ile Gln Pro Tyr Ala Glu Ser Ser
            180                 185                 190

Pro Ser Ser Glu Val Glu Thr Glu Leu Phe Ile Gly Leu Pro Arg Ser
        195                 200                 205

Ile

<210> SEQ ID NO 35
<211> LENGTH: 642
<212> TYPE: DNA
<213> ORGANISM: Brassica napus

<400> SEQUENCE: 35
atggtgaggg gcaaaactca gatgaagcga atagagaatg caacaagcag acaagtcact    60
ttctctaaac gaaggaatgg tttgctgaaa aaagcctttg agctctcagt tctttgtgat   120
gctgaagttt ctctgatcat cttctctcct aaggcaaaac tttatgaatt tgccagctcc   180
aatatgcaag ataccataga tcgttatctg aggcatacca aggatcgtgt cagcaccaaa   240
cctgtttctg aagaaaattt gcagcatttg aaacatgaag cagcaaacat gatgaagaaa   300
attgaacaac ttgaagcttc caaacgtaaa ctcttgggag aaggcatagg atcatgttcg   360
atagaggagc tgcagcaaat tgagcaacaa cttgagaaaa gtgtcaaatg tatccgagca   420
agaaagactc aagtgtttaa ggaacaaatt gagcagctca gcaaaaggag aaagctcta    480 gctgcagaaa acaagaagct cgctgaaaag tggggatctc atgaaatcga agtctggtcg   540
aataagaacc aagaaagtgg aagaggtgac gaagacagta gcccaagttc tgaagtagag   600
acagagttgt tcattgggtt accttgttct tcaagaaagt ga                       642

<210> SEQ ID NO 36
<211> LENGTH: 213
<212> TYPE: PRT
<213> ORGANISM: Brassica napus

<400> SEQUENCE: 36

Met Val Arg Gly Lys Thr Gln Met Lys Arg Ile Glu Asn Ala Thr Ser
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ser Leu Ile Ile Phe
```

```
                35                  40                  45
Ser Pro Lys Ala Lys Leu Tyr Glu Phe Ala Ser Ser Asn Met Gln Asp
    50                  55                  60

Thr Ile Asp Arg Tyr Leu Arg His Thr Lys Asp Arg Val Ser Thr Lys
65                  70                  75                  80

Pro Val Ser Glu Glu Asn Leu Gln His Leu Lys His Glu Ala Ala Asn
                85                  90                  95

Met Met Lys Lys Ile Glu Gln Leu Glu Ala Ser Lys Arg Lys Leu Leu
            100                 105                 110

Gly Glu Gly Ile Gly Ser Cys Ser Ile Glu Glu Leu Gln Gln Ile Glu
        115                 120                 125

Gln Gln Leu Glu Lys Ser Val Lys Cys Ile Arg Ala Arg Lys Thr Gln
    130                 135                 140

Val Phe Lys Glu Gln Ile Glu Gln Leu Lys Gln Lys Glu Lys Ala Leu
145                 150                 155                 160

Ala Ala Glu Asn Lys Lys Leu Ala Glu Lys Trp Gly Ser His Glu Ile
                165                 170                 175

Glu Val Trp Ser Asn Lys Asn Gln Glu Ser Gly Arg Gly Asp Glu Asp
            180                 185                 190

Ser Ser Pro Ser Ser Glu Val Glu Thr Glu Leu Phe Ile Gly Leu Pro
        195                 200                 205

Cys Ser Ser Arg Lys
    210
```

<210> SEQ ID NO 37
<211> LENGTH: 651
<212> TYPE: DNA
<213> ORGANISM: Gossypium hirsutum

<400> SEQUENCE: 37

```
atggtgaggg gaaaaacaca atgaggcgc  atagagaaca atacaagcag gcaagttaca      60
ttctcaaagc gacgaaatgg gctactaaag aaagcttttg aactatcagt tctttgtgat     120
gctgaagttg ctttaatcat cttctctcct agaggcaagc tctttgaatt tgcaagctct     180
agcatgcagc aaactataga acgttatagg cggcgtacaa aggataacga accaataag      240
ccaattgaac aaaacctgca gcatctaaag actgaatcag caaacatgtt gaagacatta     300
gaagatcttg aaatttcaag aaggaaacta cttggagaga atttgggttc atgcacactt     360
gaagaattac aagagataga acagcaatta caaagagtg  tgagcatcat cagagcaaga     420
aagcacacaa ttttcaggga ccagattgaa caattgaaag aaaaggagaa agccttagct     480
gctgaaaatg aaaagcttg  tgaaaagtgt ggaacaaaat catggaaaag attgagcgag     540
caagaagaca atgtaccgta tgacgaaagc agtccaagct cggacgttga gaccgaactg     600
ttcatcggac tgccggaagg tagaacgaga cggatcgtgc aactcaattg a              651
```

<210> SEQ ID NO 38
<211> LENGTH: 216
<212> TYPE: PRT
<213> ORGANISM: Gossypium hirsutum

<400> SEQUENCE: 38

```
Met Val Arg Gly Lys Thr Gln Met Arg Arg Ile Glu Asn Asn Thr Ser
1               5                   10                  15

Arg Gln Val Thr Phe Ser Lys Arg Arg Asn Gly Leu Leu Lys Lys Ala
            20                  25                  30
```

-continued

```
Phe Glu Leu Ser Val Leu Cys Asp Ala Glu Val Ala Leu Ile Ile Phe
         35                  40                  45

Ser Pro Arg Gly Lys Leu Phe Glu Phe Ala Ser Ser Ser Met Gln Gln
     50                  55                  60

Thr Ile Glu Arg Tyr Arg Arg Thr Lys Asp Asn Glu Thr Asn Lys
 65              70                  75                  80

Pro Ile Glu Gln Asn Leu Gln His Leu Lys Thr Glu Ser Ala Asn Met
                 85                  90                  95

Leu Lys Thr Leu Glu Asp Leu Glu Ile Ser Arg Arg Lys Leu Leu Gly
             100                 105                 110

Glu Asn Leu Gly Ser Cys Thr Leu Glu Glu Leu Gln Glu Ile Glu Gln
         115                 120                 125

Gln Leu Gln Lys Ser Val Ser Ile Ile Arg Ala Arg Lys Thr Gln Ile
         130                 135                 140

Phe Arg Asp Gln Ile Glu Gln Leu Lys Glu Lys Glu Lys Ala Leu Ala
145                 150                 155                 160

Ala Glu Asn Glu Lys Leu Cys Glu Lys Cys Gly Thr Lys Ser Trp Lys
                 165                 170                 175

Arg Leu Ser Glu Gln Glu Asp Asn Val Pro Tyr Asp Glu Ser Ser Pro
             180                 185                 190

Ser Ser Asp Val Glu Thr Glu Leu Phe Ile Gly Leu Pro Glu Gly Arg
         195                 200                 205

Thr Arg Arg Ile Val Gln Leu Asn
         210                 215
```